US006365711B1

(12) United States Patent
Whitman et al.

(10) Patent No.: US 6,365,711 B1
(45) Date of Patent: *Apr. 2, 2002

(54) METHODS AND REAGENTS FOR MODULATING TGF-β SUPERFAMILY SIGNALLING

(75) Inventors: Malcolm Whitman, Boston, MA (US); Xin Chen, Mountain View, CA (US)

(73) Assignee: President and Fellows of Harvard College, Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/087,134

(22) Filed: May 28, 1998

Related U.S. Application Data

(60) Provisional application No. 60/047,991, filed on May 28, 1997.

(51) Int. Cl.[7] .......................... C07K 14/47; C07K 14/46
(52) U.S. Cl. ........................................ 530/300; 530/350
(58) Field of Search .................................. 530/350, 300

(56) References Cited

PUBLICATIONS

Roberts and Sporn, *Peptide growth factors and their receptors I*, eds. Sporn and Roberts, Berlin, Springer–Verlage, 419–473, (1990).
Sporn, et al., Science 233: 532–534, (1986).
Brabletz et al., Mol. Cell Biol. 13: 1155–1162 (1993).
Cahouchi et al., Oncogene 11: 1615–1622 (1995).
Ausubel, et al., Current Protocols in Molecular Biology, John Wiley and Sons, New York, NY, (1994). (This publication is not provided but is available upon request of the Examiner).
Gyuris et al., Cell 75: 791–803 (1993).
Fields et al., Nature 340: 245–246 (1989).
Krieg and Melton, Meth. Enzymol. 155: 397–415 (1987).
Thomsen et al., Cell 63: 485–493 (1990).
Nieuwkoop and Faber, *Normal Table of Xenopus laevis (Daudin)*, Second Edition ed. North Holland Publishing Company, Amsterdam (1967). (This publication is not provided but is available upon request of the Examiner).
Chen et al., Nature 383: 691–696 (1996).
Turner and Weintraub, Genes and Dev. 8: 1434–1447 (1994).
LaBonne et al., Development 121: 1475–1486 (1995).
Bartel et al., Cellular Interactions in Development: A Practical Approach, Oxford Press, Oxford, 153–179.
Weller, et al., Exp. Cell Res. 221: 395–403 (1995).
LaBonne and Whitman, Development 120: 463–472 (1994).
Hartley "Cellular Interactions in Development: A Practical Approach," Oxford Press, Oxford.
Zhang et al., "Receptor–Associated MAD Homologues Synergize as Effectors of the TGF–β Response," Nature 383: 168–172 (1996).
Nakao et al., "Identification of Smad2, a Human Mad–Related Protein in the Transforming Growth Factor β Signalling Pathway," J. Biol. Chem. 272:2896–2900 (1997).
Derynck et al., "Nomenclature: Vertebrate mediators of TGFβ Family Signals," Cell 87: 173 (1996).
Lui et al., "A Human Mad Protein Acting as a BMP–Regulated Transcriptional Activator," Nature 381: 620–623 (1996).
Macias–Silva et al., "MADR2 is a Substrate of the TGFβ Receptor and its Phosphorylation is Required for Nuclear Accumulation and Signaling," Cell 87: 1215–1224 (1996).
Massague et al., Cell 69:160–1070 (1992).
Rosa, "Mix.1, a Homobox mRNA Inducible by Mesoderm Inducers, Is Expressed Mostly in the Presumptive Endodermal Cells of Xenopus Embryos," Cell 57:965–974 (1989).
Mead et al., "BMP–4—Responsive Regulation of Dorsal–Ventral Patterning by the Homobox Protein Mix.1," Nature 382:354–360 (1996).
Lagna et al., "Partnership Between DPC4 and SMAD Proteins in TGF–β Signalling Pathways," Nature 383:832–836 (1996).
Savage et al., Proc. Natl. Acad. Sci. USA 93:790–8794 (1996).
Sekelsky et al., "Genetic Characterization and Cloning of Mothers against dpp, a Gene Required for dexapentaplegic Function in Drosophila melanogaster," Genetics 139–:1347–1358 (1995).
Zhou et al. Characterization of human FAST–1, a TGF beta and activin signal transducer. Mol Cell, (Jul. 1998) 2 (1) 121–7.*
Bowie et al. Deciphering the message in protein sequences: tolerance to amino acid substitutions. Science, (Mar. 16, 1990) (4948) 1306–10.*
Ngo et al., in The Protein Folding Problem and Tertiary Structure Prediction, Merz and Le Grand (Eds), Aug. 1994, Springer Verlag, pp. 433 and 492–495.*
Chen et al. Smad4 and FAST–1 in the assembly of activin–responsive factor. Nature, (Sep. 4, 1997) 389 (6646) 85–9.*
Huang et al. Identification of a potential regulator of early transcriptional responses to mesoderminducers in the frog embryo. EMBO J., (Dec. 1, 1995) 14(23) 5965–73.*
Liu et al. Dual role of the smad4/DPC4 tumor suppressor in TGFbeta–inducible transcriptional complexes. Genes Dev Dec. 1, 1997; 11(23):3157–67.*
ATCC Cell Lines & Hybridomas. 1994. Paperback, 632 Pages, Edition No. 08, American Type Culture Collection, ISBN: 0930009541, Editor: Hay, Robert/ Chen, T. R. / Macy, Marvin / McClintock, Patrick /Reid, Yvonne / Caputo, Jane. pp. 121–122.*

* cited by examiner

*Primary Examiner*—David Romeo
(74) *Attorney, Agent, or Firm*—Medlen & Carroll, LLP

(57) ABSTRACT

FAST–1 and Smad2 or Smad3 form a complex that is specifically induced by signals generated by a TGF-β superfamily member. We have shown that a domain of FAST-1 directly interacts with Smad2 or Smad3, and that this interaction is mediated by specific domains of the two interacting molecules, namely, the MH2 domain of Smad2 or Smad3 and the Smad Interaction Domain (SID) of FAST-1. This result allows the development of methods and reagents for the isolation of compounds that are involved in, and/or modulate, TGF-β superfamily signalling.

3 Claims, 15 Drawing Sheets

Figure 5B
| Myc-Smad4 | + | + | + |
|---|---|---|---|
| GST-FAST-1 | − | + | + |
| Activin | − | − | + |
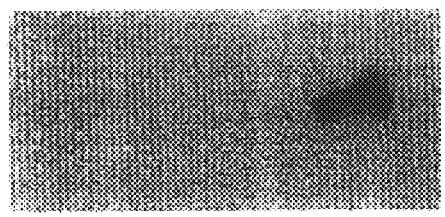
GST-IP
Myc Western
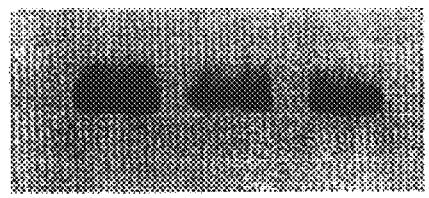
Cell lysate
Myc Western
1  2  3

```
  1  M-------------------------------------                              HUMAN FASTI PROTEIN SEQUENCE
  1  M-------------------------------------                              MOUSE FASTI PROTEIN SEQUENCE
  1  MRDPSSLYSGFPAGSQYESVEPPSLALLSS                                      XENOPUS FASTI PROTEIN SEQUENCE

2  ------------------------------                                      HUMAN FASTI PROTEIN SEQUENCE
  2  ------------------------------                                      MOUSE FASTI PROTEIN SEQUENCE
 31  IDQELPVATGQSYNHSVQPWPQPWPPPLSL                                      XENOPUS FASTI PROTEIN SEQUENCE

2  ------------------------G-----                                      HUMAN FASTI PROTEIN SEQUENCE
  2  ------------------------ASGWDLA                                     MOUSE FASTI PROTEIN SEQUENCE
 61  YREGGTWSPDRGSMYGLSPGTHEG------                                      XENOPUS FASTI PROTEIN SEQUENCE

3  -----------------------PCSGSR-                                      HUMAN FASTI PROTEIN SEQUENCE
  9  STYTPTPSPQLALAPAQGYLPCMGPRDNS                                       MOUSE FASTI PROTEIN SEQUENCE
 85  -----------------------SCTHTH-                                      XENOPUS FASTI PROTEIN SEQUENCE

9  -LGPPE--AESPSQPPKRRKKKRYLRHDKPP                                     HUMAN FASTI PROTEIN SEQUENCE
 39  QLRPPE--AESLSKTPKRRKKKRYLRHDKPP                                     MOUSE FASTI PROTEIN SEQUENCE
 91  -EGPKDSMAGDQTRSRKSKKKNYHRYNKPP                                      XENOPUS FASTI PROTEIN SEQUENCE

36  YTYLAMIALVIQAAPSRRRLKLAQII--RQVQA                                   HUMAN FASTI PROTEIN SEQUENCE
 67  YTYLAMIALVIQAAPFFRRRLKLA----QVQA                                    MOUSE FASTI PROTEIN SEQUENCE
120  YSYLAMIALVIQNSPEKRRLKLSQILKEVST                                     XENOPUS FASTI PROTEIN SEQUENCE

66  VFPFFREDYEGWKKDSIRHNLSSNRCFRKVP                                     HUMAN FASTI PROTEIN SEQUENCE
 93  VFPFFRDDYEGWKKDSIRHNLSSNRCFHKVP                                     MOUSE FASTI PROTEIN SEQUENCE
150  LFPFFNGDYMGWKDSIRHNLSSDCFKKIL                                       XENOPUS FASTI PROTEIN SEQUENCE
```

FIG. 10A

```
 96  K D P A K P Q A K G N F W A V D V S L I P A E A L R L Q N T   HUMAN FASTI PROTEIN SEQUENCE
123  K D P A K P Q A K G N F W A V D V S L I P A E A L R L Q N T   MOUSE FASTI PROTEIN SEQUENCE
180  K D P G K P Q A K G N F W T V D V S R I P L D A M K L Q N T   XENOPUS FASTI PROTEIN SEQUENCE

126  A L C R R W Q N G G A R G A F A K D L G P Y V L H - - -       HUMAN FASTI PROTEIN SEQUENCE
153  A L C R R W Q N R G T H R A F A K D I S P Y V L H - - -       MOUSE FASTI PROTEIN SEQUENCE
210  A L - - - T R G G S D Y F V Q D L A P Y I L H N Y K Y E       XENOPUS FASTI PROTEIN SEQUENCE

151  - - G R P Y R P P S P P P P P S E - - - - - - - - -           HUMAN FASTI PROTEIN SEQUENCE
178  - - G Q P Y Q P P S P P P P P R E - - - - - - - - -           MOUSE FASTI PROTEIN SEQUENCE
235  H N A G A Y G H Q M P P S H A R S L S L A E D S Q Q T N T G   XENOPUS FASTI PROTEIN SEQUENCE

166  - - G F S I K S L L R R S G E - - - - - - - - - - -           HUMAN FASTI PROTEIN SEQUENCE
193  - - G F S I K S L L G D P G K - - - - - - - - - - -           MOUSE FASTI PROTEIN SEQUENCE
265  G K L N T S F M I D S L L H D L Q E V D L P D A S - R         XENOPUS FASTI PROTEIN SEQUENCE

184  G L A P Q N S P V P A G - - - - - - - - - - - - -             HUMAN FASTI PROTEIN SEQUENCE
214  G L P G Q S T A A Q A G - - - - - - - - - - - - -             MOUSE FASTI PROTEIN SEQUENCE
291  N L E N Q R I S P A V A M N N M W S S A P L L Y T H S K P T   XENOPUS FASTI PROTEIN SEQUENCE

202  E A V P T P P L P S S E R P L W P L C P L P G P T R V E G E   HUMAN FASTI PROTEIN SEQUENCE
232  E G M G T G P S S S E T P L W P L C S L P G P T I I E G E     MOUSE FASTI PROTEIN SEQUENCE
321  R N A R S P G L S T I H S T Y - - - - S S S S S H S T I S     XENOPUS FASTI PROTEIN SEQUENCE

↙ START SID HUMAN
232  T V - - Q G G A M G P Q P S P Q S L G P - G L S T T A G H R   HUMAN FASTI PROTEIN SEQUENCE
262  S S - - Q G E V I R P S P V T P D Q G S W P L H L L E D S A   MOUSE FASTI PROTEIN SEQUENCE
347  P V G F Q K E Q E K S G R Q T Q R V G H - P I K R S R E D D   XENOPUS FASTI PROTEIN SEQUENCE
```

FIG. 10B

```
259  S S G G R S S G G H R A S - - - - - - - - - - - - - - - - - - - - - - - - - - - - - - - - - - - - - - - - - - - - - - - - - - - - - - - - - - L W G Q L    HUMAN FASTI PROTEIN SEQUENCE
290  D S R G V P R R G S R A S - - - - - - - - - - - - - - - - - - - - - - - - - - - - - - - - - - - - - - - - - - - - - - - - - - - - - - - - - - L W G Q L    MOUSE FASTI PROTEIN SEQUENCE
376  D C S T T S S D P D T G N Y S P I E P P K K M P L L S L D L                                                                                                XENOPUS FASTI PROTEIN SEQUENCE
             ↙START SID XENOPUS

277  P T S Y L P I Y T P N V V M P L A P - P - - - - - - - - - - -                                                                                              HUMAN FASTI PROTEIN SEQUENCE
308  P T S Y L P I Y T P N V V M P L A T L P - - - - - - - - - - -                                                                                              MOUSE FASTI PROTEIN SEQUENCE
406  P T S Y T K S V A P N V V A P P S V L P F F H F P R F T Y Y                                                                                                XENOPUS FASTI PROTEIN SEQUENCE
          ↙START SID MOUSE

296  - - P T S C P Q C P S - T S P A Y W G - - - - - - - - - - - V A P                                                                                          HUMAN FASTI PROTEIN SEQUENCE
328  - - T T S C P Q C P S S A S P A Y W S - - - - - - - - - - - V G T                                                                                          MOUSE FASTI PROTEIN SEQUENCE
436  N Y G P S - - - - - P Y - M T P P Y W G F P H P T N S G G D                                                                                                XENOPUS FASTI PROTEIN SEQUENCE

315  E T R G P P G L L C D L M A L F Q G V P P N K S I Y D V W V                                                                                                HUMAN FASTI PROTEIN SEQUENCE
348  E S Q G S Q D L L C D L D S L F Q G V P P N K S I Y D V W V                                                                                                MOUSE FASTI PROTEIN SEQUENCE
460  S P R G P C S P L - D L D N M L R A M P P N K S V F D V L T                                                                                                XENOPUS FASTI PROTEIN SEQUENCE

345  S H P R D L A A P G - - - - - - - - - - - - - - - - - - - - -                                                                                              HUMAN FASTI PROTEIN SEQUENCE
378  S H P R D L A A P A - - - - - - - - - - - - - - - - - - - - -                                                                                              MOUSE FASTI PROTEIN SEQUENCE
489  S H P G D L V H P S F L S Q C L G S S G S P Y P S R Q G L M                                                                                                XENOPUS FASTI PROTEIN SEQUENCE

355  - - P G W L L S W C S - - L Z                                                                                                                              HUMAN FASTI PROTEIN SEQUENCE
388  - - P G W L L S W Y S - - M Z                                                                                                                              MOUSE FASTI PROTEIN SEQUENCE
519  Y R R R P P G - - L T W S G H S M K Z                                                                                                                      XENOPUS FASTI PROTEIN SEQUENCE
```

METHODS AND REAGENTS FOR MODULATING TGF-β SUPERFAMILY SIGNALLING

PRIORITY STATEMENT

This application claims priority from United States provisional application 60/047,991, filed May 28, 1997.

STATEMENT AS TO FEDERALLY SPONSORED RESEARCH

This invention was made in part with support from the Federal government through NIH Grants Nos. HD24926 and HD29468. The Federal government has certain rights in the invention.

BACKGROUND OF THE INVENTION

TGF-β superfamily members signal through activation of transmembrane serine-threonine kinase receptors. These receptors phosphorylate and activate Smads, a novel class of signal transducers. Signals initiated by TGF-β superfamily members are important for regulating cellular processes, including cell division, survival, differentiation, and specification of developmental fate throughout the growth and development of diverse organisms.

During early embryogenesis of the frog *Xenopus laevis*, the TGF-β growth factor family plays a central role in the specification and patterning of various tissues: TGF-β superfamily members activin, Vg-1, and TGF-β all induce a full range of dorsal and ventral mesodermal markers in early embryonic tissue, whereas other TGF-β superfamily members specify axial pattern or epidermal, as opposed to neural, tissue. Almost all the critical patterning events in early Xenopus embryogenesis appear to involve members of the TGF-β superfamily.

The transforming growth factor β (TGF-β) superfamily of cytokines, which includes bone morphogenic proteins (BMPs), activin, TGF-β, and Vg-1, regulate a wide range of normal and pathological biological processes. These processes include cell specification during development, terminal differentiation of many cell types, fibrosis during wound healing or organ damage (e.g., cirrhosis), proliferation and invasiveness of normal and transformed cells, and angiogenesis and immune suppression induced by tumors (Roberts and Sporn, *Peptide growth factors and their receptors I*, eds. Sporn and Roberts, Berlin, Springer-Verlage, 419–473, 1990; Sporn et al., Science 33: 532–534, 1986). For example, one member of the family, TGF-β, is secreted by a wide variety of tumors and has a wide variety of immunosuppressive effects, including the ability to induce apoptosis in B and T lymphocytes (Brabletz et al., Mol. Cell Biol. 13: 1155–1162, 1993; Cahouchi et al., Oncogene 11: 1615–1622, 1995; Weller et al., Exp. Cell Res. 221: 395–403, 1995). The ability to manipulate specific aspects of TGF-β superfamily signalling in vivo would be a powerful tool both for understanding the role of these factors in normal embryonic patterning and for controlling a broad range of pathological processes.

SUMMARY OF THE INVENTION

We have discovered methods and reagents for identifying compounds that modulate TGF-β superfamily signalling. These methods and compounds are useful for the detection and treatment of conditions involving abnormal TGF-β superfamily signalling.

In the first four aspects, the invention provides methods for detecting compounds capable of modulating TGF-β superfamily signalling. The methods include the steps of providing a cell having a reporter gene operably linked to a DNA-binding-protein recognition site, in addition to having either:

a) a first fusion gene capable of expressing a first fusion protein comprising a polypeptide fragment of Smad2 covalently bonded to a binding moiety capable of specifically binding to the DNA-binding-protein recognition site and a second fusion gene capable of expressing a second fusion protein comprising a polypeptide fragment of FAST-1 covalently bonded to a gene activating moiety, b) a first fusion gene capable of expressing a first fusion protein comprising a polypeptide fragment of FAST-1 covalently bonded to a binding moiety capable of specifically binding to the DNA-binding-protein recognition site and a second fusion gene capable of expressing a second fusion protein comprising a polypeptide fragment of Smad2 covalently bonded to a gene activating moiety, c) a first fusion gene capable of expressing a first fusion protein comprising a polypeptide fragment of Smad3 covalently bonded to a binding moiety capable of specifically binding to the DNA-binding-protein recognition site and a second fusion gene capable of expressing a second fusion protein comprising a polypeptide fragment of FAST-1 covalently bonded to a gene activating moiety, or d) a first fusion gene capable of expressing a first fusion protein comprising a polypeptide fragment of FAST-1 covalently bonded to a binding moiety capable of specifically binding to the DNA-binding-protein recognition site and a second fusion gene capable of expressing a second fusion protein comprising a polypeptide fragment of Smad3 covalently bonded to a gene activating moiety; exposing the cell to the compound; and measuring reporter gene expression in the cell, where a change in the reporter gene expression indicates that the compound is capable of modulating TGF-β superfamily signalling.

In the fifth, sixth, seventh, and eighth aspects, the invention features a cell useful for detecting a compound capable of modulating TGF-β superfamily signalling, the cell having a reporter gene operably linked to a DNA-binding-protein recognition site in addition to having either:

a) a first fusion gene capable of expressing a first fusion protein comprising a polypeptide fragment of Smad2 covalently bonded to a binding moiety capable of specifically binding to the DNA-binding-protein recognition site and a second fusion gene capable of expressing a second fusion protein, the second fusion protein comprising a polypeptide fragment of FAST-1 covalently bonded to a gene activating moiety, b) a first fusion gene capable of expressing a first fusion protein comprising a polypeptide fragment of FAST-1 covalently bonded to a binding moiety capable of specifically binding to the DNA-binding-protein recognition site and a second fusion gene capable of expressing a second fusion protein, the second fusion protein comprising a polypeptide fragment of Smad2 covalently bonded to a gene activating moiety, c) a first fusion gene capable of expressing a first fusion protein comprising a polypeptide fragment of Smad3 covalently bonded to a binding moiety capable of specifically binding to the DNA-binding-protein recognition site and a second fusion gene capable of expressing a second fusion protein, the second fusion protein comprising a polypeptide fragment of FAST-1 covalently bonded to a gene activating moiety, or d) a first fusion gene capable of expressing a first fusion protein comprising a polypeptide fragment of FAST-1 covalently bonded to a binding moiety capable of specifically binding to the DNA-binding-protein recognition site and a second fusion gene capable of expressing a second fusion protein, the second fusion protein comprising a polypeptide fragment of Smad3 covalently bonded to a gene activating moiety.

In preferred embodiments of the first eight aspects of the invention, a decrease in reporter gene expression indicates a compound that is capable of inhibiting TGF-β superfamily signalling, and an increase in reporter gene expression indicates a compound that is capable of enhancing TGF-β superfamily signalling. In other embodiments of these aspects of the invention, reporter gene expression may be assayed by a color reaction or assayed by cell viability. In still another embodiment of the first eight aspects of the invention, the cell may be a yeast cell.

In the ninth, tenth, eleventh, and twelfth aspects, the invention provides a method for detecting a compound capable of modulating TGF-β superfamily signalling. The method comprises the steps of providing a first polypeptide comprising a polypeptide fragment of FAST-1, providing a second polypeptide, the second polypeptide comprising a polypeptide fragment of either Smad2 or Smad3 (or alternatively, providing a first polypeptide comprising a polypeptide fragment of Smad2 or Smad3, and providing a second polypeptide comprising a polypeptide fragment of FAST-1), exposing the first polypeptide to the second polypeptide and to the compound, and measuring the level of interaction between the first polypeptide and the second polypeptide, wherein an alteration in the level of interaction indicates that the compound is capable of modulating TGF-β superfamily signalling.

In one preferred embodiment of the ninth, tenth, eleventh, and twelfth aspects of the invention, at least one of the first polypeptide or the second polypeptide is immobilized on a solid-phase substance. In another preferred embodiment, a decrease in the level of interaction indicates that the compound is capable of inhibiting TGF-β superfamily signalling, and an increase in the level of interaction indicates that the compound is capable of enhancing TGF-β superfamily signalling. In other embodiments of the ninth, tenth, eleventh, and twelfth aspects, the first polypeptide is produced by a cell that contains a first fusion gene capable of expressing the first polypeptide, and the second polypeptide is produced by a cell that contains a second gene capable of expressing the second polypeptide.

In various preferred embodiments of all of the above aspects of the invention, the polypeptide fragment of FAST-1 consists of, at maximum, Xenopus FAST-1 amino acids 380 to 506, human FAST-1 amino acids 234 to 365, and mouse FAST-1 amino acids 309 to 398. In other preferred embodiments of all of the aspects of the invention, the polypeptide fragment of Smad2 consists of, at maximum, Smad2 amino acids 248 to 467 or 274 to 467, and the polypeptide fragment of Smad3 consists of, at maximum, Smad3 amino acids 230 to 446, amino acids 253 to 446, amino acids 230 to 424, or amino acids 253 to 424.

In the thirteenth aspect, the invention features a polypeptide comprising a polypeptide fragment of FAST-1. In a preferred embodiment of this aspect of the invention, the polypeptide fragment of FAST-1 includes, at maximum, Xenopus FAST-1 amino acids 380 to 506, or fragments thereof, human FAST-1 amino acids 234 to 365, or fragments thereof, or mouse FAST-1 amino acids 309 to 398, or fragments thereof.

In the fourteenth, fifteenth, sixteenth, and seventeenth aspects, the invention features a method for detecting a compound capable of modulating TGF-β superfamily signalling, comprising providing a reporter gene operably linked to a DNA-binding-protein recognition site and additionally providing either:

a) a first fusion protein comprising a polypeptide fragment of FAST-1 covalently bonded to a binding moiety capable of specifically binding to the DNA-binding-protein recognition site and a second fusion protein comprising a polypeptide fragment of Smad2 covalently bonded to a gene activating moiety, b) a first fusion protein comprising a polypeptide fragment of Smad2 covalently bonded to a binding moiety capable of specifically binding to the DNA-binding-protein recognition site and a second fusion protein comprising a polypeptide fragment of FAST-1 covalently bonded to a gene activating moiety, c) a first fusion protein comprising a polypeptide fragment of FAST-1 covalently bonded to a binding moiety capable of specifically binding to the DNA-binding-protein recognition site and a second fusion protein comprising a polypeptide fragment of Smad3 covalently bonded to a gene activating moiety, or d) a first fusion protein comprising a polypeptide fragment of Smad3 covalently bonded to a binding moiety capable of specifically binding to the DNA-binding-protein recognition site and a second fusion protein comprising a polypeptide fragment of FAST-1 covalently bonded to a gene activating moiety;

exposing the first fusion protein to the second fusion protein, to the reporter gene, and to the compound; and measuring the reporter gene expression, a change in the reporter gene expression indicating a compound that is capable of modulating TGF-β superfamily signalling.

In various preferred embodiments of the fifteenth, sixteenth, seventeenth, and eighteenth aspects, a change in reporter gene expression that is a decrease indicates a compound that is capable of inhibiting TGF-β superfamily signalling, and a change in the reporter gene expression that is an increase in the reporter gene expression indicates a compound that is capable of enhancing TGF-β superfamily signalling. In other embodiments, the polypeptide of FAST-1 includes Xenopus FAST-1 amino acids 380 to 506, or fragments thereof, human FAST-1 amino acids 234 to 365, or fragments thereof, or mouse FAST-1 amino acids 309 to 398, or fragments thereof; the polypeptide fragment of Smad2 includes Smad2 amino acids 248 to 467, or fragments thereof; and the polypeptide fragment of Smad3 includes Smad3 amino acids 230 to 424, or fragments thereof. In yet another embodiment, providing the first fusion protein comprises providing a first fusion gene capable of expressing the first fusion protein and providing the second fusion protein comprises providing a second fusion gene capable of expressing the second fusion protein.

In the nineteenth aspect, the invention provides a method for diagnosing a mammal having or likely to develop a disorder involving abnormal TGF-β superfamily signalling. The method includes determining whether the mammal has a mutation in a gene encoding FAST-1. In a preferred embodiment of this aspect, the mutation is in the Smad Interaction Domain (SID).

In the twentieth aspect, the invention provides methods for diagnosing a mammal having or likely to develop a disorder involving abnormal TGF-β superfamily signalling comprising determining whether the mammal has an altered level of expression of FAST-1.

In preferred embodiments of the nineteenth and twentieth aspects of the invention, the disorder is a developmental disorder, and the mammal is a human, and may be a fetus.

In the twentieth aspect, the invention features a substantially pure mammalian FAST-1 protein or polypeptide fragment thereof for use in modulating TGF-β superfamily signalling.

In preferred embodiments of the twentieth aspect, the protein or polypeptide fragment may be from a human or a rodent. In other preferred embodiments, the polypeptide fragment comprises the Smad Interaction Domain (SID). In still another preferred embodiment, the polypeptide fragment binds to Smad2 or Smad3.

In a twenty-first aspect, the invention features a substantially pure polypeptide fragment comprising the Smad Interaction Domain (SID) of FAST-1 from Xenopus, for use in modulating TGF-β superfamily signalling.

In related, twenty-second, twenty-third, and twenty-fourth aspects, the invention features substantially pure polypeptides or fragments thereof having about 50% or greater amino acid sequence identity, about 75% or greater amino acid sequence identity, and about 90% or greater amino acid sequence identity to the comparable amino acid sequence of the mammalian FAST-1 protein or polypeptide fragment thereof. Preferably, the identity is determined by comparison with the FAST-1 SID (i.e., FAST-1 amino acids 380 to 509 of Xenopus FAST-1, amino acids 234 to 365 of human FAST-1, or amino acids 309 to 398 of mouse FAST-1). In another preferred embodiment, the polypeptide fragment binds to Smad2 or Smad3.

In a twenty-fifth aspect, the invention features a substantially pure nucleic acid encoding a mammalian FAST-1 protein or polypeptide fragment thereof.

In a twenty-sixth aspect, the invention features a vector containing a nucleic acid of the twenty-fifth aspect, capable of directing expression of the protein or polypeptide fragment thereof.

In a twenty-seventh aspect, the invention features a substantially pure nucleic acid encoding a FAST-1 Smad Interaction Domain (SID).

In a twenty-eighth aspect, the invention features a cell containing the vector of the twenty-sixth and twenty-seventh aspects above.

In a twenty-ninth aspect, the invention features a method of modulating TGF-β superfamily signalling in a cell, comprising providing a cell intracellularly with a substantially pure FAST-1 protein, or polypeptide fragment thereof, wherein the FAST-1 protein or polypeptide fragment is sufficient to modulate TGF-β superfamily signalling in a cell.

In a thirtieth aspect, the invention features a method of modulating TGF-β superfamily signalling in a cell, comprising introducing, into a cell, a vector comprising a nucleic acid encoding FAST-1 protein, or polypeptide fragment thereof, wherein the vector is capable of directing expression of the protein or polypeptide fragment in a cell containing the vector, and wherein expression of the FAST-1 protein or polypeptide fragment is sufficient to modulate TGF-β superfamily signalling in a cell.

In preferred embodiments of the twenty-ninth and thirtieth aspects, the signalling may be decreased or increased.

"Reporter gene" means any gene that encodes a product whose expression is detectable. Such genes include, without limitation, lacZ, amino acid biosynthetic genes, for example, the yeast LEU2, HIS3, LYS2, TRP1, or URA3 genes, nucleic acid biosynthetic genes, the mammalian chloramphenicol transacetylase (CAT) gene or GUS gene, or any surface antigen for which specific antibodies are available. Reporter genes may encode any enzyme that provides a phenotypic marker, for example, a protein that is necessary for cell growth or a toxic protein leading to cell death, or gene encoding a protein detectable by color assay or whose expression leads to an absence of color. Other preferred reporter genes are those encoding fluorescent markers, such as the green fluorescent protein (GFP)-encoding gene, or reporter genes encoding enzymes whose activity may be detected by chemiluminescence, such as luciferase. Reporter genes may facilitate either a selection or a screen for reporter gene expression, and quantitative differences in reporter gene expression may be measured as an indication of interaction affinities.

"Covalently bonded" means that two domains are joined by covalent bonds, directly or indirectly. That is, the "covalently bonded" proteins or protein moieties may be immediately contiguous or may be separated by stretches of one or more amino acids within the same fusion protein.

"Protein" or "polypeptide" or "polypeptide fragment" means any chain of more than two amino acids, regardless of post-translational modification (e.g., glycosylation or phosphorylation), constituting all or part of a naturally-occurring polypeptide or peptide, or constituting a non-naturally occurring polypeptide or peptide.

"Smad2 protein or polypeptide fragment thereof" means a Smad2 protein (or polypeptide fragment or domain thereof) found in Xenopus or mammalian (e.g. mouse or human) cells. A preferred domain of Smad2 is the Mad Homology 2 (MH2) domain (i.e., amino acids 274 to 467 of human or Xenopus Smad2). Also preferred are polypeptide fragments comprising the MH2 domain, that consist of, at maximum, amino acids 274 to 467 or amino acids 248 to 467 of human or Xenopus Smad2, or the corresponding amino acids that comprise Smad2 MH2 domains from other species. These polypeptide fragments are capable of interacting with the FAST-1 Smad Interaction Domain (SID).

"Smad3 protein or polypeptide fragment thereof" means a Smad3 protein (or polypeptide fragment or domain thereof) found in Xenopus or mammalian (e.g. mouse or human) cells. A preferred domain of Smad3 is the Mad Homology 2 (MH2) domain (i.e., amino acids 253 to 446 of human Smad3). Also preferred are polypeptide fragments comprising the MH2 domain, that consist of, at maximum, human Smad3 amino acids 230 to 446, and subfragments thereof, consisting of, at maximum, amino acids 253 to 446, amino acids 253 to 424, or amino acids 230 to 424, or the corresponding amino acids that comprise Smad3 MH2 domains from other species. These polypeptide fragments are capable of interacting with the FAST-1 SID domain.

"Mammalian FAST-1 protein or polypeptide fragment thereof" means an amino acid sequence derived from a mammalian cell which displays at least 30%, preferably, 40%, more preferably 50%, still more preferably 60%, 70%, or even 80% means amino acid sequence identity to a FAST-1 Smad Interaction Domain (SID), i.e., amino acids 380 to 506 of the Xenopus FAST-1 protein, amino acids 234 to 365 of the human FAST-1 protein, or amino acids 309 to 398 of the mouse FAST-1 protein. The length of comparison, generally will be at least 16 amino acids, preferably at least 20 amino acids, more preferably at least 25 amino acids, and most preferably at least 30 amino acids. Preferably, a mammalian FAST-1 protein, or polypeptide fragment thereof, is able to bind Smad2. The FAST-1 SID is a preferred polypeptide fragment of FAST-1.

"Operably linked" means that a gene and one or more regulatory sequences are connected in such a way as to permit gene expression when the appropriate molecules (e.g., transcriptional activator proteins) are bound to the regulatory sequences.

"Binding moiety" means a stretch of amino acids which is capable of directing specific polypeptide binding to a particular DNA sequence (i.e., a "protein binding site").

"Modulatory compound" or "modulating compound", as used herein, means any compound capable of either increasing or decreasing the amount of signalling initiated by a TGF-β superfamily member.

"Substantially pure protein" or substantially pure polypeptide" means a protein or polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is a xenopus or mammalian, e.g. human or mouse, FAST-1 polypeptide, or polypeptide fragment thereof, that is at least 75%, more preferably at least 90%, and most preferably at least 99%, by weight, pure. A substantially pure mammalian, e.g. human or mouse, FAST-1 polypeptide, or polypeptide fragment may be obtained, for example, by extraction from a natural source (e.g. a fibroblast, neuronal cell, or lymphocyte) by expression of a recombinant nucleic acid encoding a FAST-1 polypeptide, or by chemically synthesizing the protein. Purity can be measured by any appropriate method, e.g., by column chromatography, polyacrylamide gel electrophoresis, or HPLC analysis.

A polypeptide is substantially free of naturally associated components when it is separated from those contaminants which accompany it in its natural state. Thus, a polypeptide which is chemically synthesized or produced in a cellular system different from the cell from which it naturally originates will be substantially free from its naturally associated components. Accordingly, substantially pure polypeptides include those which naturally occur in eukaryotic organisms but are synthesized in *E. coli* or other prokaryotes.

"Substantially pure nucleic acid" means nucleic acid that is free of the genes which, in the naturally-occurring genome of the organism from which the nucleic acid of the invention is derived, flank the gene. The term therefore includes, for example, a recombinant nucleic acid that is incorporated into a vector; into an autonomously replicating plasmid or virus; or into the genomic nucleic acid of a prokaryote or eukaryote; or that exists as a separate molecule (e.g., a cDNA or a genomic or cDNA fragment produced by PCR or restriction endonuclease digestion) independent of other sequences. It also includes a recombinant nucleic acid that is part of a hybrid gene encoding additional polypeptide sequence.

By "Substantially identical" means a polypeptide or nucleic acid exhibiting at least 75%, preferably 85%, more preferably 90%, and most preferably 95% identity to a reference amino acid or nucleic acid sequence. For polypeptides, the length of comparison will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

Default settings of sequence analysis software programs employ parameters that are considered, by those of skill in the art, to yield biologically significant results; i.e., an alignment of two polypeptides that shows one or more amino acid stretches having a high percentage of sequence identity represents two polypeptides that share a functional relationship. For example, FAST-1 polypeptides are identified by virtue of their possessing an amino acid sequence that displays at least 30% identity to a FAST-1 SID.

BRIEF DESCRIPTION OF THE DRAWINGS

FIG. 5B shows a Western blot of whole lysates and anti-GST co-immunoprecipitates from Xenopus embryos co-microinjected with RNA encoding GST-FAST-1 and Myc-Smad4 (Myc-DPC4), plus or minus RNA encoding activin, demonstrating that Smad4 co-precipitates with FAST-1 in an activin-dependent manner.

FIGS. 10A, 10B, and 10C show an amino acid sequence alignment of human (SEQ ID NO:19), mouse (SEQ ID NO:20, and Xenopus (SEQ ID NO:21) FAST-1.

DETAILED DESCRIPTION OF THE INVENTION

It is now demonstrated that the interactions of a FAST-1 polypeptide fragment with Smad2 and Smad3 polypeptide fragments in vivo as well as in vitro are clearly involved in TGF-β superfamily signalling pathways in eukaryotic cells.

In *Xenopus laevis* embryos, Smad2 is a component of the activin responsive factor (ARF) complex that binds to the ARE promoter element of the Mix.2 gene. The major DNA binding component of the ARF is a novel winged helix transcription factor that we have named FAST-1. In the present invention, we show that Smad4 is present in ARF, and that FAST-1, Smad4, and Smad2 co-immunoprecipitate in an activin-regulated fashion. We have mapped the site of interaction between FAST-1 and Smad2/Smad4 to a novel C-terminal domain of FAST-1; overexpression of this domain specifically inhibits activin signalling.

Figure 1:
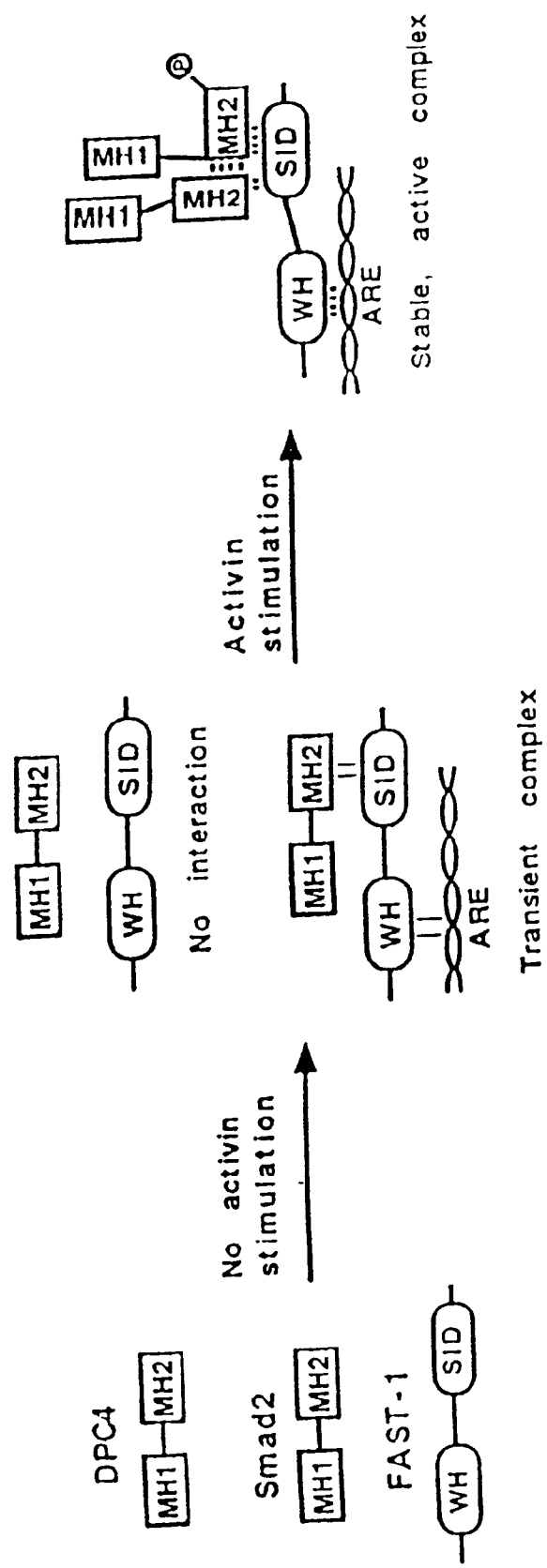
FIG. 1 shows a schematic diagram indicating the interactions between FAST-1, Smad2, and DPC4 (Smad4) in ARF formation. WH and SID indicate the winged helix region and the Smad Interaction Domain of FAST-1, respectively.

In a yeast 2-hybrid assay, the FAST-1 C-terminus was found to directly interact with Smad2, but not Smad4. Furthermore, we can detect binding of the FAST-1 C-terminus to the MH2 domain of Smad2 in vitro. The results of these findings have allowed us to propose the model for ARF formation shown in FIG. 1.

The interaction of FAST-1 and Smad2 domains provided in the present invention allows the identification of compounds capable of modulating the effects of TGF-β superfamily signalling and the identification of patients who either have or are likely to develop disorders involving abnormal TGF-β superfamily-mediated signal transduction.

I. Uses for the Invention

The methods and compounds provided in the invention allow modulation and simulation of the signalling pathways of TGF-β superfamily members. These methods and compounds may provide a means to detect treatments and to possibly treat or cure individuals with a variety of diseases, including, without limitation, developmental disorders, immunological disorders, and cancer. The invention also describes methods by which individuals may be identified who either have or are likely to develop disorders involving abnormal TGF-β superfamily signalling.

II. FAST-1, Smad2, and Smad3 Fragments

We have found that polypeptide fragments comprising various portions of the FAST-1, Smad2 and Smad3 proteins have been useful in identifying the domains important for the interaction of FAST-1 (SEQ ID NO: 11, 14, and 17) with either Smad2 (SEQ ID NO: 2 and 5) or Smad3 (SEQ ID NO: 8). Methods for generating such fragments are well known in the art (see, for example, Ausubel et al., *Current Protocols in Molecular Biology*, John Wiley & Sons, New York, N.Y., 1994) and are further described herein. For example, a Smad2 polypeptide fragment may be generated by amplifying the desired fragment by the polymerase chain reaction (PCR) using oligonucleotide primers designed according to the published Smad2 nucleic acid sequence (SEQ ID NO: 1 and 4). Preferably the oligonucleotide primers comprise unique restriction enzyme sites which facilitate insertion of the DNA fragment into the cloning site of a eukaryotic expression vector. Furthermore, the Smad2 fragment may be tagged with an epitope (e.g., hemagglutinin (HA) or GST) by cloning the fragment into a epitope fusion expression vector. The Smad2 fragment-bearing vector is then introduced into a prokaryotic or eukaryotic cell by artifice, using the various techniques known in the art and described herein, which result in the production of the Smad2 polypeptide fragment. Similar techniques using FAST-1 (SEQ ID NO: 10, 13, and 16) and Smad3 (SEQ ID NO: 7) nucleic acid sequences are employed to generate FAST-1 and Smad3 polypeptide fragments.

In one approach, FAST-1 and Smad2, or Smad3 polypeptide fragments may be used to evaluate the portions of these proteins involved in regulation of TGF-β signalling during *Xenopus laevis* embryogenesis. In particular, polypeptide fragments comprising the domains of the FAST-1, Smad2, and Smad3 proteins responsible for the interaction of FAST-1 with either Smad2 or Smad3 may be used to induce TGF-β superfamily signalling, or to prevent TFG-β superfamily signalling.

III. Screens for Compounds Which Modulate TGF-β Superfamily Signalling

FAST-1 and Smad2 or FAST-1 and Smad3 may be used to facilitate the identification of compounds that increase or decrease TGF-β superfamily-mediated signal transduction. In one approach, compounds that modulate the signals generated by the TGF-β superfamily are detected by screening for compounds that alter the physical interaction between the FAST-1 SID domain (SEQ ID NO: 12, 15, and 18) and the Smad2 (SEQ ID NO: 3 and 6) or Smad3 (SEQ ID NO: 9) MH2 domain. These compounds are detected by adapting yeast two-hybrid expression systems known in the art for use as described herein. These systems which allow detection of protein interactions via a transcriptional activation assay, are generally described by Gyuris et al. (Cell 75:791–803, 1993) and Fields et al. (Nature 340:245–246, 1989), and are commercially available from Clontech (Palo Alto, Calif.).

In this approach, a region of FAST-1, which we have discovered interacts with Smad2, is fused to the GAL4-DNA-binding domain by subcloning a DNA fragment encoding this, the FAST-1 Smad Interaction Domain (SID), into the expression vector, pGBT9, provided in the MATCH-MAKER Two-Hybrid System kit commercially available from Clontech (catalog number K1605-1). A fusion of the GAL4 activation domain with the MH2 domain of Smad2 or Smad3 (which interacts with the FAST-1 SID) is generated by subcloning the Smad2 or Smad3 MH2 domain-encoding DNA fragment into the expression vector, PGAD424, also provided in the Clontech kit. Analogous expression vectors may also be used. Yeast transformations and colony lift filter assays are carried out according to the methods of MATCH-MAKER Two-Hybrid System and various methods known in the art. Prior to the colony filter assay, transformed yeast may be treated with candidate compounds being screened for the ability to modulate TGF-β signalling. The interaction results obtained using the candidate compound in combination with the yeast system may then be compared to those results observed with the yeast system not treated with the candidate compound, all other factors (e.g., cell type and culture conditions) being equal. A compound capable of modulating TGF-β superfamily-mediated signalling is able to alter the interaction between the Smad2 or Smad3 MH2 domain and the FAST-1 SID.

In another embodiment of this approach, a compound capable of decreasing TGF-β superfamily signalling by disrupting the binding of the Smad2 (or Smad3) MH2 to the FAST-1 SID may be isolated using the modified yeast-two hybrid system described above, in which the reporter gene encodes a protein, such as ricin, that is toxic to yeast. Yeast cells containing such a ricin reporter gene die unless the binding of Smad2 MH2 to FAST-1 SID is disrupted. Yeast cells treated with a compound that disrupts the Smad2/FAST-1 interaction form viable colonies, and from this result it may be inferred that the compound is capable of decreasing, and possibly inhibiting, signals initiated by members of the TGF-β superfamily.

In another approach, compounds capable of inhibiting signalling by TGF-β and other members of the TGF-β superfamily may be identified in vitro using assays that detect disruption of the in vitro binding of FAST-1 SID to the Smad2 (or Smad3) MH2 domain. For example, in order to detect FAST-1/Smad interactions, the FAST-1 SID domain is fused to glutathione S-transferase (GST) by subcloning the FAST-1 SID-encoding DNA fragment into a bacterial expression vector that encodes a GST tag. Such vectors are well known in the art and are commercially available (e.g., the pGEX fusion vectors commercially available from Pharmacia). GST-tagged FAST-1 SID fusion protein is produced by transforming the GST-FAST-1 SID-encoding vector into *E. coli* bacteria. Fusion proteins are then purified by allowing the proteins from lysed bacteria to bind to glutathione sepharose-coated beads. The GST-tagged FAST-1 SID-bearing beads are then used to specifically bind Myc-tagged Smad2 (or Smad3) MH2 domains polypeptides produced in Xenopus embryos. Detection of FAST-1/Smad2 (or Smad3) interactions are assessed by resolving the glutathione-immobilized proteins by Laemmli gel electrophoresis and subjecting the resolved proteins to Western blot analysis using anti-Myc antibodies.

In order to detect compounds that inhibit TGF-β superfamily signalling by disrupting FAST-1/Smad2 (or Smad3) interactions, Xenopus embryo lysates containing Myc-tagged Smad2 (or Smad3) MH2 domain polypeptides are incubated with a candidate TGF-β signalling modulatory compound prior to the incubation with glutathione Sepharose-coated beads carrying the GST-tagged FAST-1 SID. Glutathione-immobilized proteins from treated vs. untreated Xenopus embryo lysates are then subjected to Western blotting with anti-Myc antibodies. A difference in the amount of anti-Myc reactivity of the glutathione-immobilized proteins from treated samples vs. untreated samples indicates that the test compound modulates TGF-β superfamily-mediated signal transduction.

GST-tagged FAST-1 SID fusion proteins may be immobilized on a solid-state substance for rapid high-throughput identification of compounds that modulate TGF-β superfamily signalling. Preferably, the solid-state substance is the bottom of a well on a 96-well (or similar) plate. Each well may then be provided with a known amount of the MH2 domain of either Smad2 or Smad3 that is tagged with a readily detectable epitope (e.g., an short polypeptide fragment, e.g., HA or Myc, that is specifically recognized by an antibody). Preferably, a Smad2 or Smad3 MH2 domain tagged with the alkaline phosphatase (AP) enzyme is added to each GST-tagged FAST-1 SID-bearing well. Candidate compounds to be screened for an ability to modulate TGF-β superfamily signalling are then added individually or in combination to each well on the plate. After allowing the interaction of the components in each well, the plate is washed, and the substrate for AP is added to each well. A compound that modulates TGF-β superfamily signalling may affect the binding affinities of the FAST-1 SID and the Smad2 or Smad3 MH2 such that the amount of bound Smad MH2, and hence, bound AP enzymatic activity, is altered. Preferable AP substrates are colorimetric substrates, such as the nitro blue tetrazolium (NBT) and 5-bromo-1-chloro-3-indolyl-phosphate (BCIP) reagents that are commercially available (e.g., from Promega).

After allowing formation of the blue/black precipitate to occur in a control well that has not been treated with a candidate compound, the plate is quantitated for color intensity on a 96-well plate reader. A compound that affects the color intensity of AP substrates when added to a well, as compared to a well not treated with a compound, indicates a compound that has the ability to modulate TGF-β superfamily mediated signal transduction.

Molecules that are found to effectively modulate TGF-β superfamily signalling, using the methods described above, may be further tested using in vivo animal models. Compounds that function effectively in an in vivo setting may be used as therapeutics to either inhibit or enhance TGF-β superfamily member-mediated signalling, as appropriate.

IV. Administration of Modulators of TGF-β Superfamily Signal Transduction

A TGF-β superfamily signalling modulator may be administered within a pharmaceutically-acceptable diluent, carrier, or excipient, in unit dosage form. Conventional pharmaceutical practice may be employed to provide suitable formulations or compositions to administer a TGF-β superfamily signalling modulator(s) to patients suffering from a disease (e.g., a developmental disease) that is caused by an abnormal amount of TGF-β superfamily member-mediated signal transduction. Administration may begin before the patient is symptomatic. Any appropriate route of administration may be employed, for example, administration may be parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for TGF-β superfamily signalling modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Dosage is determined by standard techniques and is dependent, for example, upon the weight of the patient and the type or extent of disorder being treated.

V. Diagnostics for Disorders involving Abnormal TGF-β Superfamily Signalling To determine whether an individual either has or is likely to develop a disorder (e.g., a developmental disorder) involving abnormal TGF-β superfamily signalling, that individual may be screened for mutations in the domains (e.g., the SID of FAST-1 or the MH2 domains of Smad2 and Smad3) of the genes encoding FAST-1, Smad2, and Smad3 that mediate the binding interactions of FAST-1 with Smad2 or Smad3. Screening for mutations may be carried out using any standard technique including, without limitation, methods involving sequencing, or mismatch binding or cleaving assays. For example, a nucleic acid sample may be derived from cells of an individual to be tested for a mutation (for example, by PCR amplification), and the FAST-1, Smad2, and Smad3 genes may be subjected to rapid sequence analysis by automated sequencing techniques using primers generated from FAST-1, Smad2, and Smad3 sequences described in the art and herein.

Alternatively, an individual who either has or is likely to develop a disorder involving abnormal TGF-β superfamily signalling may be screened for altered expression of FAST-1, Smad2 or Smad3. Such assays may be carried out, for example, using any standard nucleic acid-based assay (e.g., Northern blot analysis) or immunological assay (e.g., enzyme-linked immunosorbent assay (ELISA)), preferably in a high through-put assay format. For example, cells may be obtained from an individual to be tested, and analyzed by ELISA for the expression of FAST-1, Smad2, or Smad3 proteins, using as probes, fluorophore-tagged antibodies directed against these proteins. Individuals that have altered protein levels relative to the general population, are readily identified using such ELISA-based assays.

VI. FAST-1 Related Genes

Standard techniques, such as the polymerase chain reaction (PCR) and DNA hybridization, may be used to clone additional FAST-1 homologues in other species. In order to detect such homologues, genomic DNA of various organisms (e.g., humans or mice) may be analyzed by Southern blotting using nucleic acid probes generated from the nucleic acid sequences encoding Xenopus FAST-1. Hybridization at low stringency should reveal bands that correspond to DNA encoding FAST-1 and/or related family members. Xenopus FAST-1 nucleic acid probes may be based upon the codon preference of the organism, whose DNA is under analysis, or they may be degenerate probes based upon all possible codon combinations, or they may be a combination of codon preference and codon degeneracy. Such probes may also be used to screen either genomic or cDNA libraries for sequences that hybridize to the probe. FAST-1 nucleic acid probes also may be used as primers to clone additional FAST-1 related genes by RT-PCR, using methods known in the art.

Another method for identifying mammalian homologues of the FAST-1 is by searching publically available databases for sequences that share sequence identity with the Xenopus FAST-1 nucleic acid or amino acid sequence (Genbank accession number U70980), or with sequence fragments thereof. A particularly preferred FAST-1 sequence fragment is the sequence corresponding to the Smad Interaction Domain (SID) of FAST-1. Once identified, a candidate mammalian homologue of FAST-1 (or polypeptide fragment thereof) may be tested for FAST-1-like activity (e.g., ability to bind the Smad2 or Smad3 MH2 domain), using the assays described herein.

The following examples are meant to illustrate the invention. They are not meant to limit the invention in any way.

EXAMPLE I

Smad4 (DPC4) is a Component of ARF

Signalling by TGF-β superfamily members induces transcriptional activation of target genes. Some of these transcriptional responses are necessary and sufficient for the specification or patterning of mesoderm. Several TGF-β superfamily-responsive genes show immediate-early responses, ie., they are induced even when translation is inhibited by cycloheximide. Two such genes, Mix.1 and Mix.2, are transcriptionally activated by signals initiated by TGF-β superfamily members such as activin, Vg-1, TGF-β, and BMP4. In contrast, Mix.1 and Mix.2 are not transcriptionally activated by non-TGF-β mesoderm inducers or axial modifiers.

An activin-responsive factor (ARF) was identified using an electrophoretic mobility-shift assay (EMSA) for embryonic proteins that bind to the Mix.2 promoter elements. The ARF, which is induced in embryonic blastomeres after 5–30 minutes of activin stimulation, binds specifically to a 50-bp Mix.2 promoter element. FAST-1 was identified as the major DNA-binding component of the ARF complex.

Smad2, which associates in a ligand regulated manner with another member of the Smad family, Smad4 (DPC4), is a compound of the ARF complex. Therefore, we asked whether Smad4 is also a component of ARF.

Methods

HA-tagged Smad4 was provided by Akiko Hata and Joan Massague, and the untagged full length Smad4 construct was provided by P. Hoodless and J. Wrana. We have previously described the Xenopus activin encoding construct (Thomsen et al., Cell 63: 485–493). These constructs were in vitro transcribed according to standard techniques described in, for example, Krieg and Melton (Meth. Enzymol. 155: 397–415, 1987).

Figure 2:
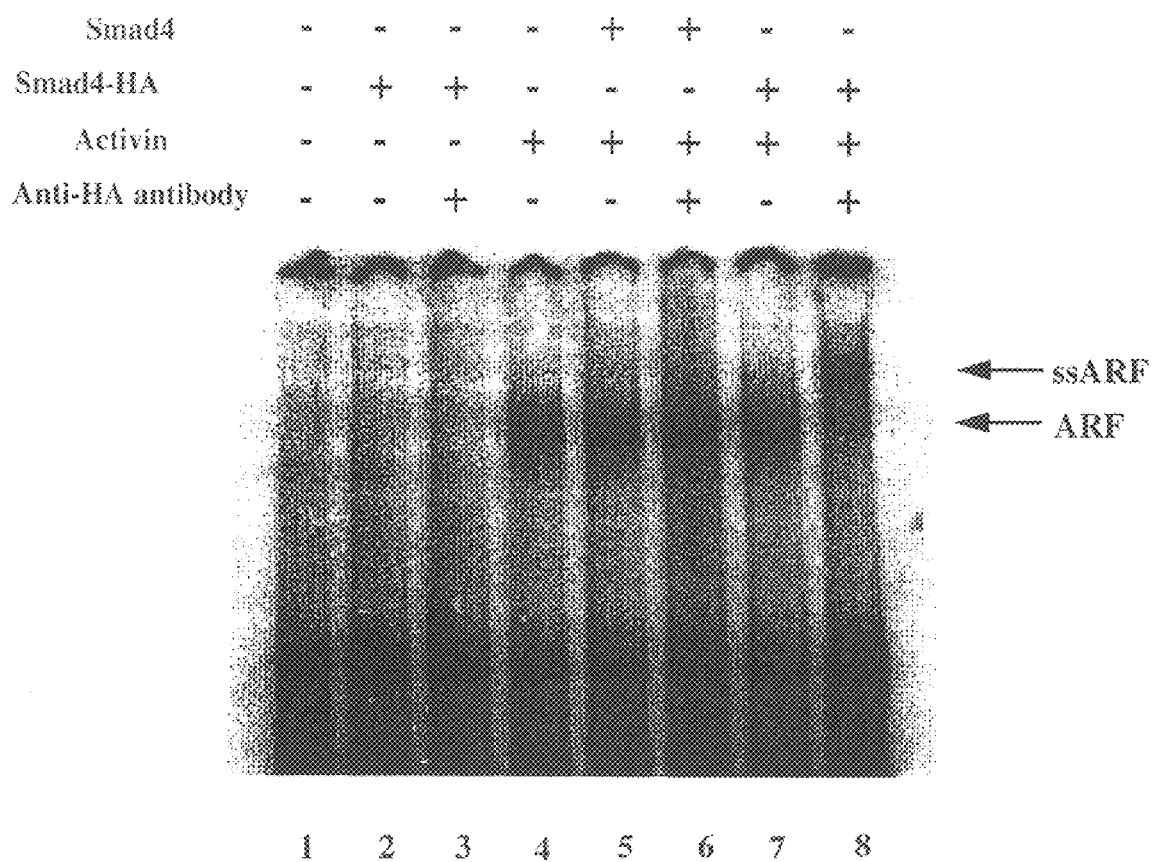
FIG. 2 shows a supershifted electrophoretic mobility-shift assay (EMSA) demonstrating the incorporation of Smad4 into the ARF complex.

*Xenopus laevis* embryos at the 2-cell stage were microinjected in both blastomeres with 0.5–2 ng of RNA encoding HA-tagged or untagged Smad4 (DPC4) with or without RNA encoding activin, as indicated in FIG. 2. Embryos were maintained in 1×MMR containing 3% Ficoll during microinjection, after which embryos were transferred to 0.1×MMR. Embryos were harvested for EMSA lysates at Stage 9 as previously described (Huang et al., EMBO J 14:5965–5973, 1995). Staging of embryos was done according to Nieuwkoop and Faber (*Normal Table of Xenopus laevis* (Daudin), Second edition ed. North Holland Publishing Company, Amsterdam, 1967).

EMSA was performed as previously described (Huang et al., supra) using as a probe the $^{32}$P-labeled ARE from the Mix.2 promoter (Chen, et al., *Nature* 383:691–696, 1996). For supershift assays, EMSA assay mixtures were incubated with anti-HA antibody (commercially available from Gibco-BRL) for 1 hour on ice prior to SDS-PAGE and autoradiography.

Results

FIG. 2 shows a supershifted electrophoretic mobility-shift assay (EMSA) demonstrating the incorporation of Smad4 into the ARF complex. HA-tagged (lanes 2, 3, 7, and 8) or untagged (lanes 5 and 6) Smad4 was expressed in early Xenopus embryos and incorporation of HA-tagged protein into ARF was tested by co-incubation of EMSA mixtures with anti-HA antibody (lanes 3, 6, and 8). "Activin" indicates samples in which activin was co-expressed. "ssARF" (super-shifted ARF) indicates increased mobility of the anti-HA antibody-bound ARF.

The EMSA experiment of FIG. 2 shows that Smad4 (DPC4) is a component of the ARF complex. A supershift of the ARF complex by anti-HA antibody is dependent upon the presence of HA-Smad4 within the embryo lysate (FIG. 8, lane 2). However, overexpression of Smad4 in the absence of stimulation by activin is not sufficient for ARF formation, since supershifts were detected only in embryos co-injected with HA-Smad4 RNA plus activin RNA, but not in embryos injected with HA-Smad4 RNA alone. Hence, the binding of ligand (in this case, activin) to a TGF-β superfamily receptor appears to provide additional signals that are necessary for ARF formation.

EXAMPLE II

Smad4 (DPC4) and Smad2 Co-associate in ARF Complexes

Incorporation of Smad4 (DPC4) into ARF might reflect the co-association of Smad2, Smad4, and FAST-1 within the same complex. Alternatively, there might be two types of ARF: a Smad2-containing ARF, which would predominate in the presence of overexpressed Smad2, and a Smad4-containing ARF, which would predominate in the presence of overexpressed Smad4. We next determined which of these two models was correct.

Methods

Xenopus Smad2 (provided by J. Graff and D. Melton) carrying six consecutive Myc epitope tags at the Smad2 N-terminus was generated by cloning the Smad2 coding region into the fusion vector pCS2(+)MT, which encodes the Myc tags (Thomsen et al., Cell 63: 485–493, 1990; Turner and Weintraub, Gen. and Dev. 8: 1434–1447, 1994). Smad3 was similarly N-terminally fused to six Myc tags.

RNAs encoding Myc-tagged Smad2, HA-tagged Smad4, and activin were co-injected into two-cell Xenopus laevis embryos according to the method described in Example I. Stage 9 embryos were harvested and assayed by supershift-EMSA with anti-Myc or anti-HA antibodies as described in Example I.

Results

Figure 3:
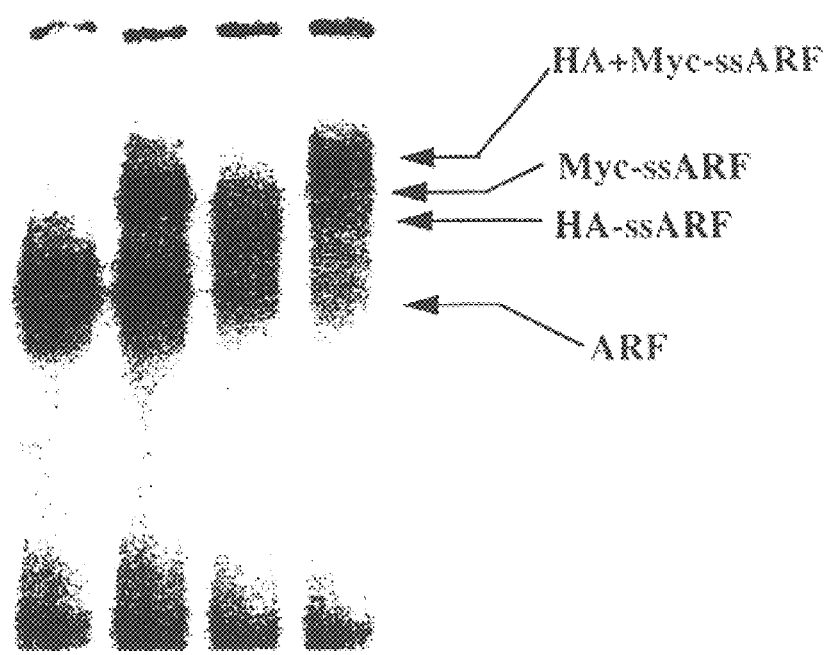
FIG. 3 shows a supershifted EMSA demonstrating the presence of Smad2 and Smad4 within the same ARF complex.

FIG. 3 shows a supershifted EMSA demonstrating the presence of Myc-tagged Smad2 and HA-tagged Smad4 within the same ARF complex. ARF complexes that were supershifted using only anti-HA antibody are designated "HA-ssARF", those using only anti-Myc antibody, "Myc-ssARF", and those that were supershifted using both antibodies are designated HA+Myc-ssARF.

The addition of both anti-HA and anti-Myc antibodies resulted in a more highly supershifted ARF, relative to supershifted ARFs produced by either antibody alone. This result strongly suggests that Smad2 and Smad4 co-exist within the same ARF complex, rather than within two discrete subsets of ARF complexes. We obtained identical results Myc-tagged Smad3 in place of Myc-tagged Smad2. Consistent with these results, we observed that the simultaneous addition of anti-HA and anti-Myc antibodies to lysates from embryos expressing HA-tagged Smad4 plus untagged Smad2, or Myc-tagged Smad2 plus untagged Smad4, resulted in supershifted complexes analogous to those produced by using only one anti-epitope antibody.

EXAMPLE III

The Smad2 MH2 Domain Alone can be Incorporated into the ARF Complex

The Smad2 Mad Homology 2 (MH2) domain is necessary for Smad2-dependent transcriptional activation. In order to determine whether the MH2 domain is also necessary for incorporation of Smad2 into the ARF, we used supershift-EMSA to ask whether the Smad2 MH2 domain alone could be incorporated into ARF complexes.

Methods

The Smad2 MH2 domain was tagged with the FLAG epitope by PCR-amplifying a DNA sequence encoding the Smad2 MH2 domain (Smad2 amino acids 248–467) and subcloning the PCR product into the pCS2+vector (previously described by Thomsen et al., Cell 63: 485–493, 1990; and Turner and Weintraub, Gen. and Dev. 8: 1434–1447, 1994).

FLAG-tagged Smad2 MH2, HA-tagged Smad4, and activin were co-expressed in two-cell Xenopus laevis embryos according to the method described in Example I. Stage 9 embryos were harvested and assayed for incorporation into the ARF by supershift-EMSA using anti-FLAG or anti-HA antibodies, as described in Example I.

Results

Figure 4:
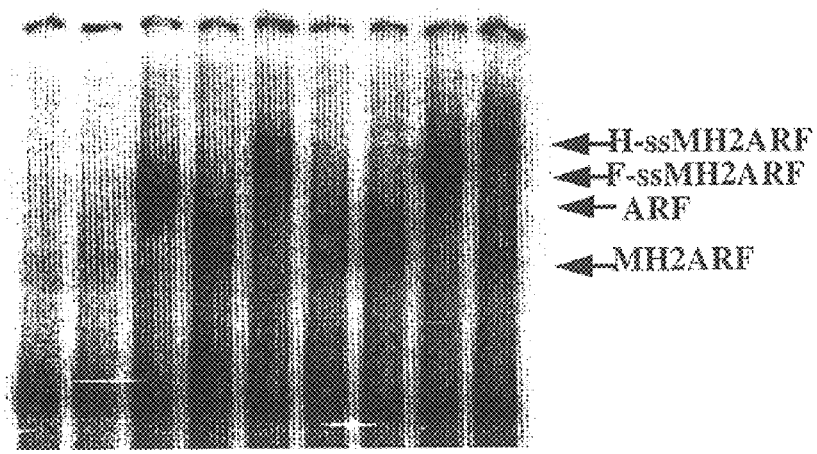
FIG. 4 shows a supershifted EMSA demonstrating that the Smad2/MH2 domain alone can be incorporated into the ARF complex.

FIG. 4 shows a supershifted EMSA demonstrating that the Smad2 MH2 domain alone can be incorporated into the ARF. ARF complexes that have increased mobility due to the incorporation of Smad2-MH2 (rather than full-length Smad2) are indicated by "MH2-ARF", FLAG-Smad2-MH2-ARF complexes supershifted with anti-FLAG are indicated by "FLAG-ssMH2ARF", and Smad2-MH2-ARF complexes supershifted by anti-HA (recognizing Smad4 in the complex) are indicated by "HA-ssMH2ARF".

The Smad2 MH2 domain was part of a complex that bound ARE, but that migrated more rapidly than did endogenous ARF (presumably due to the reduced molecular weight of complexes containing the Smad2 MH2 domain as opposed to full-length Smad2 (FIG. 4). Incorporation of the Smad2 MH2 domain into ARF was activin-dependent (FIG. 4, lanes 2 and 4). ARF complexes that contain the Smad2 MH2 domain are supershifted by anti-HA antibody, indicating that these complexes also contain HA-tagged Smad4 (FIG. 4, Lane 9).

EXAMPLE IV

Co-immunoprecipitation of FAST-1 with Smad2

In the experiments described in the previous examples, EMSA was used to detect the binding of ARF to its DNA target, ARE. To study FAST-1/Smad2 interactions in the absence of ARF/ARE complex formation, we asked whether FAST-1 and Smad2 could be co-immunoprecipitated from Xenopus embryo lysates.

Methods

Myc-tagged Smad1 was generated by subcloning the sequences encoding Smad1 from the FLAG-tagged Smad1 construct into the pCS2(+)MT vector, which is a modification of the pCS2+vector originally described in Thomsen et al., supra and Turner and Weintraub, supra. FAST-1 was tagged by N-terminal fusion at amino acid 61 with GST.

Xenopus laevis embryos at the 2-cell stage were co-injected either with RNA encoding GST-tagged FAST-1 plus RNA encoding Myc-tagged Smad1, or with RNA encoding GST-tagged FAST-1 plus RNA encoding Myc-tagged Smad2, both plus or minus co-injection of RNA encoding activin.

Embryos were harvested at Stage 9 in lysate buffer (as described in Example I), and cleared by centrifugation for 15 minutes at 32,000×g. Cleared lysates were immunoprecipitated with anti-GST tag antibody for 1 hr at 4° C., and then incubated with protein A-sepharose for 30 min. The beads were then washed under the following conditions: 1×lysate buffer 0.1% NP40, 1×lysate buffer+0.4M NaCl, 1×lysate buffer+0.5% NP40, 1×lysate buffer+0.2M NaCl, 0.25% NP40, 1×lysate buffer. Samples were fractionated by electrophoresis and transferred to nitrocellulose. The nitrocellulose-immobilized immunoprecipitates were blotted with anti-Myc antibody and immunoreactive bands were detected by ECL as previously described (see LaBonne et al., Development 121: 1475–1486, 1995). In parallel, whole-embryo lysates were also subjected to electrophoresis, transferred to nitrocellulose, blotted with anti-Myc antibody, and subjected to ECL detection.

Results

Figure 5A:
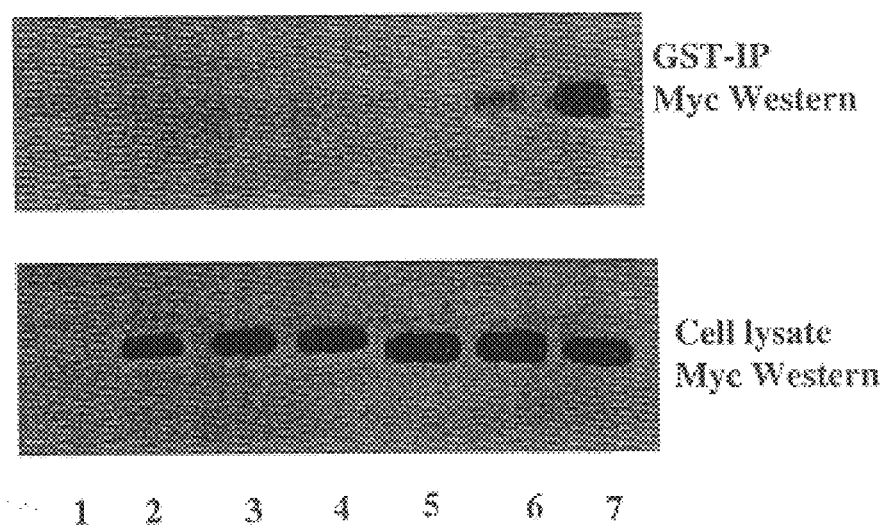
FIG. 5A shows a Western blot of whole lysates and anti-GST co-immunoprecipitates from Xenopus embryos co-microinjected with RNA encoding GST-FAST-1 and Myc-Smad1 or Myc-Smad2, plus or minus RNA encoding activin, demonstrating that Smad2 but not Smad1 co-precipitates with FAST-1 in an activin-stimulated manner.

As shown in FIG. 5A, Myc-tagged Smad2 co-immunoprecipitated with GST-tagged FAST-1, and Smad2/FAST-1 complex formation was enhanced by activin stimulation (lanes 6 and 7). The anti-GST antibody did not immunoprecipitate Myc-tagged Smad2 from lysates of embryos not expressing GST-tagged FAST-1, indicating that Smad2 immunoprecipitation resulted from its specifically interacting with FAST-1.

In contrast to Smad2 and FAST-1, co-expression of tagged Smad1 and FAST-1 did not lead to detectable co-immunoprecipitation of Smad-1 (FIG. 5A, lanes 3 and 4). Equivalent expression of Smad1 and Smad2 in embryos was confirmed by Western analysis of whole embryonic lysate (FIG. 5A, lower panel). Therefore, it appears that Smad1 and FAST-1 do not directly interact, or do not interact as strongly as do Smad2 and FAST-1.

Ligand-induced activation of TGF-β superfamily receptors is apparently not a prerequisite for Smad2/FAST-1 complex formation: Myc-tagged Smad2 co-immunoprecipitated with FAST-1 even in the absence of stimulation by activin, although Smad2/FAST-1 complex formation increased in lysates from embryos injected with activin mRNA. At high levels of FAST-1 expression, Smad2 co-precipitation was nearly equivalent in lysates from activin-stimulated and unstimulated embryos (similar results were obtained using Myc-tagged Smad3 in place of Smad2, or by first immunoprecipitating Smad2 and then detecting co-immunoprecipitated FAST-1 by Western blot analysis).

We were surprised to observe the activin-independent co-precipitation of Myc-Smad2 and GST-FAST-1, since EMSA experiments described in previous examples showed that supershifting of ARF/ARE complexes by anti-Myc (i.e. Myc-Smad2) antibody was activin-dependent. This result suggests that in addition to the activin-dependent formation of FAST-1/Smad2-containing complexes that are competent for DNA binding, there exist activin-dependent complexes that are either not competent for DNA binding, or not stable under our EMSA assay conditions.

EXAMPLE V

Co-precipitation of FAST-1 with Smad4 (DPC4)

In order to study the nature of FAST-1/Smad4 (DPC4) interacterations prior to ARE/ARF complex formation, we asked whether Smad4 and FAST-1 could be co-immunoprecipitated from activin-stimulated and unstimulated Xenopus embryo lysates.

Methods

Myc-tagged Smad4 was constructed by cloning the full-length Smad4 into the pCS2(+)MT vector, which is described in Example II.

Myc-tagged Smad4 was co-expressed with GST-tagged FAST-1 in Xenopus embryos in the presence or absence of activin stimulation. The microinjected embryos were lysed, GST-tagged FAST-1 was immunoprecipitated with anti-GST antibody, and immunoprecipitates were subjected to Western blot analysis using anti-Myc antibody, as described in Example IV.

Results

Myc-tagged Smad4 (DPC4) was co-immunoprecipitated with GST-tagged FAST-1 from lysates of activin-stimulated embryos. However, such Smad4/FAST-1 complexes were not evident above background in lysates from unstimulated embryos (FIG. 5B). Identical results were obtained by immunoprecipitating Myc-tagged Smad4 and performing immunoblots using an anti-GST (GST-FAST-1) antibody, or by substituting FLAG-tagged FAST-1 for GST-tagged FAST-1. Hence, the association of Smad4 with FAST-1 requires prior activin stimulation.

EXAMPLE VI

Deletion Analysis of FAST-1

FAST-1 contains a predicted winged helix DNA binding domain, but has no extensive homologies to other winged helix factors or other known proteins outside the DNA binding domain. To identify the regions of FAST-1 that are important for its incorporation into ARF, we expressed epitope-tagged deletion mutants of FAST-1 in early embryos and tested them for incorporation into ARF by antibody supershift-EMSA.

Methods

FAST-1 was tagged by N-terminal fusion at amino acid 61 with 6 Myc tags, by cloning FAST-1 cDNA encoding amino acids 61 to 534 into the pCS2(+)MT vector (see Example II) to generate the Myc-tagged 61–534 FAST construct. The Myc-tagged Δ1–366 FAST-1 construct was generated by cloning FAST-1 cDNA encoding amino acids 366 to 534 into the pCS2(+)MT vector.

Various deletion mutants of FAST-1 were constructed from the Myc-tagged FAST 61–534: Myc-tagged Δ516–534; Myc-tagged Δ506–534; Myc-tagged Δ473–534; Myc-tagged Δ281–366; Myc-tagged Δ366–380; Myc-tagged Δ366–407; Myc-tagged Δ207–453; Myc-tagged Δ366–473; Myc-tagged Δ366–534; Myc-tagged Δ380–407; and Myc-tagged Δ453–506. Messenger RNAs encoding the Myc-tagged FAST-1 deletion mutants plus mRNA encoding activin were microinjected into two-cell Xenopus laevis embryos. Stage 9 embryos were harvested for EMSA as described in Example I, and the ability of anti-Myc antibodies to supershift ARF/ARE complexes was assessed.

Messenger RNAs encoding FAST-1 deletion mutants also were co-microinjected either with RNA encoding Myc-tagged Smad2 plus or minus RNA encoding activin, or with RNA encoding HA-tagged Smad4 (DPC4) plus RNA encoding activin, and EMSA lysates were prepared from stage 9 embryos. ARF/ARE complexes that were supershifted by anti-Myc- or anti-HA-specific antibodies indicated FAST-1 deletion mutants that retained the ability to associate with Smad2 or Smad4, respectively.

Results

In order to determine which regions of FAST-1 interact with Smad2 and Smad4 and which are necessary for incorporation into ARF and for ARF/ARE complex formation, mRNAs encoding epitope-tagged FAST-1 deletion mutants were co-expressed with tagged Smad2 or Smad4 plus or minus activin. The summarized results of these experiments are shown in FIG. 6A, and FAST-1 polypeptide domains that are necessary for interactions with Smads and for ARF/ARE complex formation are shown in FIG. 6B (TAG=Myc tag; amino acids 108–219 delineate the winged helix domain).

Deletions N-terminal to the forkhead domain (N-terminal to FAST-1 amino acid 107) do not appear to reduce incorporation of FAST-1 into ARF. Moreover, deletion of the N-terminal two-thirds of FAST-1 (up to amino acid 365), including the entire winged helix domain, does not reduce ligand-dependent association of FAST-1 with Smad2 or Smad4 and, hence, does not reduce incorporation of FAST-1 into ARF.

Figure 6A:
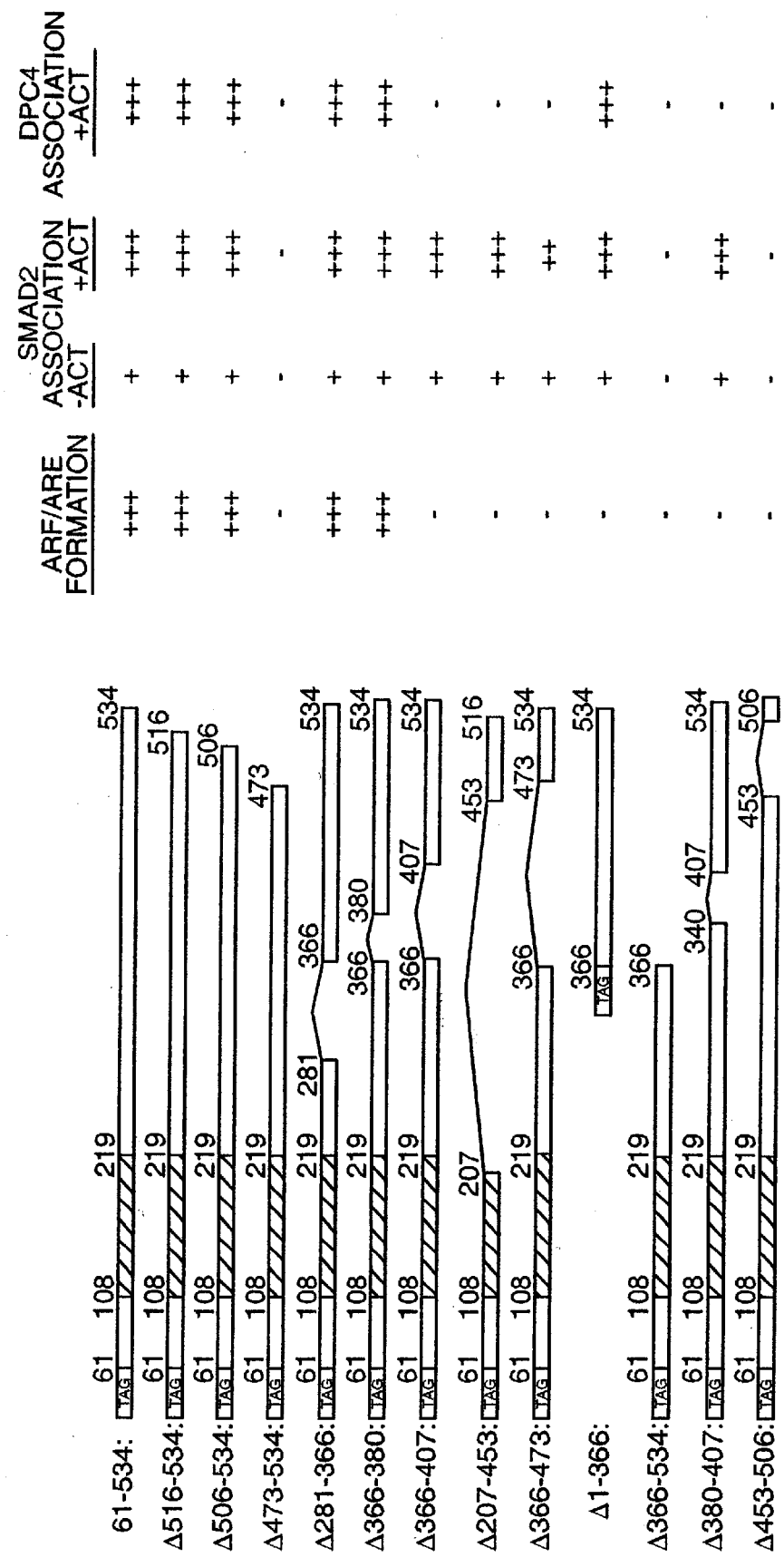
FIG. 6A shows a summary of experiments that tested the ability of Myc-tagged FAST-1 deletion mutants to become incorporated into the ARF/ARE complexes or to associate with Smad2 in an activin-dependent and -independent manner.
Figure 6B:
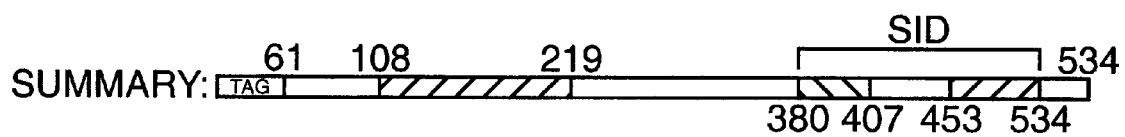
FIG. 6B is a diagram of Myc-tagged FAST-1 showing the Smad Interaction Domain (SID) and the winged helix domain (amino acids 108–219).

However, as shown in FIG. 6A, FAST-1 deletion mutants that lack the winged helix DNA-binding domain are not incorporated into ARF/ARE complexes. These data show that the winged helix domain is not necessary for FAST-1/Smad interactions and for FAST-1 incorporation into the ARF, but is necessary for ARF/ARE complex formation.

Deletions from the N-terminal side of the C-terminal half of FAST-1, up to amino acid 380 (e.g., Δ281–366), also allowed association of FAST-1 with Smad2 or Smad4 in an activin-dependent manner, as did a 29-amino acid C-terminal deletion. However, deletion of an additional 33 C-terminal amino acids prevented association of FAST-1 with Smad2 or Smad4. Although deletions of the C-terminus beyond the C-terminal 29 amino acids prevents FAST-1 incorporation into ARF, such deletions do not affect the ARE-binding activity of FAST-1 itself.

The FAST-1 domain responsible for co-precipitation with Smad2 or Smad4 localizes to a 126 amino acid C-terminal domain (380–506); this domain also is necessary for incorporation of FAST-1 into ARF/ARE complexes. We call this region of FAST-1 the Smad Interaction Domain (SID). Additional FAST-1 deletions (Δ207–453, Δ506–518, and Δ473–518) allowed us to delimit the region necessary for activin-dependent association of FAST-1 and Smad2 to amino acids 453–506. Experiments using a construct with a deletion (Δ366–473) from the N-terminal side of the SID showed that amino acids C-terminal to position 473 are sufficient for reduced, but still significant, activin-dependent association of FAST-1 with Smad2, but are insufficient for mediating interactions with Smad4, or for ARF/ARE complex formation.

Comparison of the regions of FAST-1 necessary for ARF/ARE formation with those regions necessary for co-immunoprecipitation with Smad2 and with Smad4 revealed a subregion of the FAST-1 SID (amino acids 380–407) that was necessary for activin-dependent ARF/ARE complex formation, but not necessary for the co-precipitation of Smad2 with FAST-1. However, this region was necessary for the co-immunoprecipitation of Smad4 with FAST-1. This finding, in combination with the observation that there were no deletion mutants of FAST-1 that co-immunoprecipitated with Smad4 but not with Smad2 in an activin-independent manner, suggests that Smad2 and FAST-1 initially interact in an activin-independent manner (i.e., prior to engagement of the TGF-β receptor by ligand), and that activin-stimulated phosphorylation of the Smad2 C-terminus enhances the association between the Smad2 MH2 domain and the region of FAST-1 encompassing amino acids 453–506, as determined from experiments using mutants Δ366–407, Δ380–407, and Δ207–453. This activin-dependent step allows Smad4 to interact with Smad2 and FAST-1.

Although FAST-1/Smad2 interaction occurs in the absence of Smad4 binding of the FAST-1/Smad2 complex to the ARE is not observed for FAST-1 mutants that are unable to bind Smad4. Hence, interaction among Smad4, Smad2, and a FAST-1 domain encompassing amino acids 380–407 is necessary for the formation of stable ARF/ARE complexes.

To summarize, the FAST-1 SID appears to possess two subdomains that mediate the sequential association of FAST-1 with Smad2, which then associate with Smad4; ARF complexes must contain these three factors in order to stably bind the ARE.

EXAMPLE VII

Yeast-Two Hybrid Interaction of FAST-1 with Smads

The activin-stimulated co-precipitation of FAST-1 with Smad2 and Smad4 demonstrated that these polypeptides are able to form a complex in the absence of the ARE DNA target, but did not address whether additional components of the activin signalling pathway are necessary for complex formation. In order to directly examine the physical interactions among Smad2, Smad4, and FAST-1, we tested these proteins for association in a yeast interaction trap system (Fields, supra). Portions of FAST-1 or Smad4 cloned into a GAL4 DNA binding domain fusion vector (pGBT9) were tested for their ability to interact with various Smad-GAL4 activator domain (pGAD424) fusions.

Methods

Interaction trap constructs: Truncated derivatives of FAST-I and Smad genes were cloned into the shuttle/expression vectors pGBT9 and pGAD424 (or pGAD10) (Bartel et al., *Using the two-hybrid system to detectprotein—protein interactions*, p153–179. In D. Hartley (ed.), *Cellular Interactions in Development: A Practical Approach*, Oxford Press, Oxford). A fusion of the GAL4-DNA-binding domain in the pGBT9 vector with each FAST-1 truncation derivative was generated, as was a fusion of the GAL4 activation domain in the pGAD424/pGAD 10 vector with each Smad.

Specifically, FAST-1-GAL4 DNA-binding domain fusion proteins in the pGBT9 vector included the following regions of FAST-1: (1) FAST-1 N-domain and C-domain (aa61 to aa516); (2) FAST-1 C-terminus (aa366 to aa518); (3) FAST-1 Δ207–453 (aa61 to aa515, with 6 Myc epitope tags at the junction with the GAL4-DNA-binding domain, with aa207 to aa453 deleted); (4) FAST-1 Δ366–407 (aa61 to aa515, with aa366 to aa407 deleted); (5) FAST-1 Δ366–439 (aa61 to aa515, with aa366 to aa439 deleted); (6) FAST-I forkhead domain (aa56 to aa365).

Smad-GAL4 activation domain fusion proteins in the pGAD424 or pGAD10 vector were generated that included the following Smad regions: (1) Xenopus Smad2 MH2 domain (aa248 to aa467); (2) human Smad1 MH2 domain (aa249 to aa465); (3) full-length mouse Smad4 (aa1 to aa548); (4) mouse Smad4 MH2 domain (aa306 to aa548). In addition, full-length Smad4 (aa1 to aa548) and the MH2 domain of Smad4 (aa306 to aa548) were cloned into the pGBT9 vector.

Transformation and testing of yeast with two-hybrid clones: Yeast transformations, colony lift filter assays were carried out according to the MATCHMAKER Two-Hybrid System protocol (Clontech Laboratories, Inc., Palo Alto, Calif.). For the filter assay, colony color was periodically observed during a 5–6 hour incubation at 30° C. following initial exposure of permeabilized yeast to the Z buffer/X-gal solution. The liquid culture beta-galactosidase assay was performed according to the MATCHMAKER Two-Hybrid System protocol (Clontech Laboratories, Inc., Palo Alto, Calif.). O-nitrophenyl beta-D-galactopyranoside (ONPG) was used as a substrate in this assay. Beta-galactosidase units corresponding to each sample were calculated using the following equation: Beta galactosidase units=(1000× $OD_{420}$)÷(tV×$OD_{600}$) where: t=elapsed time (in minutes) of incubation, V=0.1 ml X concentration factor of 5, $OD_{600}$= Absorbance at 600 nm of 300 microliters of Z buffer-washed and resuspended culture.

Positive results were measured either as the development of blue color on X-Gal filter lifts of colonies expressing both activator and DNA binding domain constructs relative to colonies expressing each construct alone, or as a ratio of β-galactosidase activity in liquid cultures expressing activator and DNA binding domain constructs relative to colonies containing the DNA binding domain construct alone.

Results

As shown in Table 1, the C-terminal third of FAST-1, to which the Smad2 co-immunoprecipitation function of FAST-1 mapped (FAST-1 366–518), interacted strongly with the MH2 domain of Smad2, whereas the winged helix domain region (FAST-1 56–365), did not. The Smad2 MH2 domain, and Smad4 itself (in pGAD424, the activator domain construct) interacted with Smad4 when Smad4 was expressed in pGBT9 (DNA binding domain construct), confirming that the activator domain-Smad2 and-Smad4 fusion proteins were expressed, and that these proteins physically interact within the yeast assay. In contrast, the C-terminus of FAST-1 did not interact detectably with the MH2 domain of Smad1, confirming the specificity of its interaction with the Smad2 MH2 domain. Nor did the FAST-1 C-terminus interact detectably with the MH2 domain of Smad4.

Additional N-terminal deletions of the C-terminal third of FAST-1 which allowed us to distinguish regions necessary for ARF/ARE complex formation and Smad4 association from those necessary for Smad2 co-immunoprecipitation (i.e., FAST-1Δ366–407), showed that the region of FAST-1 necessary for its interaction with Smad2 in yeast was similar to the FAST-1 region necessary for FAST-1/Smad2 co-immunoprecipitation. Although our results from the yeast interaction trap assay the possibility that additional proteins enhance Smad4/FAST-1 interactions (for example, yeast lack homologues for the activin signalling pathway), our results indicate that activin signalling is not a prerequisite for Smad2/FAST-1 interaction.

TABLE 1

Interactions of Smads with Themselves and FAST-1

| Bait Construct | Interactor Construct | Color Intensity (Filters) |
| --- | --- | --- |
| FAST-I (aa6l-518) | Smad2 (MH2) | + |
| | Smad1 (MH2) | − |
| | Smad4 (Full Length) | − |
| | Smad4 (MH2) | − |
| FAST-1 (aa366-518) | Smad2 (MH2) | + |
| | Smad1 (MH2) | − |
| | Smad4 (Full Length) | − |
| | Smad4 (MH2) | − |
| FAST-L (aa56-365: Δ366-518) | Smad2 (MH2) | − |
| | Smad1 (MH2) | − |
| FAST-I (aa6l-515: Δ366-407) | Smad2 (MH2) | + |
| | Smad1 (MH2) | − |
| FAST-I (aa6l-515: Δ366-439) | Smad2 (MH2) | + |
| | Smad1 (MH2) | − |
| FAST-I (aa6l-515: Δ207-453) | Smad2 (MH2) | + |
| | Smad1 (MH2) | − |
| Smad4 (FL) | Smad2 (MH2) | + |
| | Smad1 (MH2) | + |
| | Smad4.(Full Length) | + |
| Smad2 (MH2) | Smad4 (MH2) | + |

EXAMPLE VIII

Overexpressed FAST-1 SID Domains Blocks Formation of the ARF

The identification of a domain in FAST-1 that is necessary for interaction with Smads raised the possibility of using this domain to competitively inhibit activin signalling. Embryos were injected with mRNA encoding amino acids 366–518 of FAST-1 (the C-terminal third of FAST-1, containing the SID) and tested for their ability to respond to activin signals. We first asked whether the FAST-1 SID could inhibit activin-dependent ARF/ARE complex formation.

Methods

Two ng of mRNA encoding FAST-1 amino acids 366 to 518, plus or minus mRNA encoding activin, was co-injected into both blastomeres of two-cell *Xenopus laevis* embryos by the method described in Example I. Stage 9 embryos were harvested and tested for ARF/ARE complex formation by EMSA as described in Example I.

Results

Figure 7:
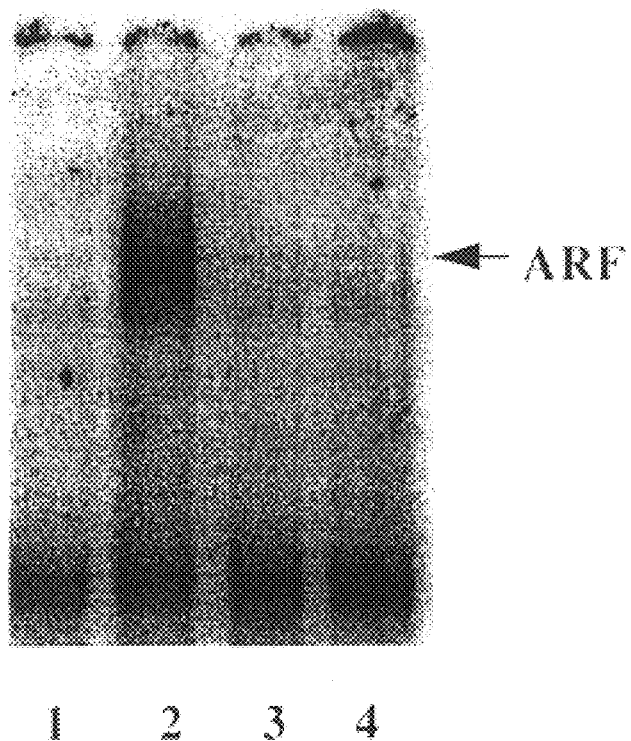
FIG. 7 shows an EMSA demonstrating the inhibition of ARF/ARE complex formation by overexpression of the FAST-1 SID.

Control embryos (FIG. 7, lanes 1, 2) and embryos injected with mRNA encoding FAST-1 366–518 (FIG. 7, lanes 3, 4) plus (FIG. 7, lanes 2, 3) or minus (FIG. 7, lanes 1, 4) activin stimulation were harvested at Stage 9 and lysates were tested for ARF/ARE complex formation by EMSA. As shown in FIG. 7, overexpression of the Smad Interaction Domain of FAST-1 inhibited the formation of ARF/ARE complexes.

EXAMPLE IX

Overexpression of FAST-1 SID Blocks Brachyury Induction and Animal Cap Induction by Activin The activin/TGFβ superfamily induces mesoderm formation in early Xenopus embryos. Induction of mesoderm may be inferred by the detection of brachyury, a marker of early mesoderm, and by animal cap elongation.

We tested the effect of FAST SID overexpression upon activin-induced brachyury expression, and upon activin-induced animal cap elongation.

Methods

Animal cap assays and RT-PCR: Two ng of mRNA encoding the FAST-1 SID (FAST-1 amino acids 366 to 518) and/or 150 pg Smad2 RNA were microinjected into both blastomeres of two-cell *Xenopus laevis* embryos by the method described in Example I. Animal caps were cut from Stage 8–9 blastulae and cultured in 0.7×MMR containing 0.1% gelatin, 100 μg/ml BSA, 250 μg/ml Gentamicin (GIBCO BRL), and 200 pM purified recombinant activin (Ajinomoto, Inc.), or 100 ng/ml human recombinant bFGF (GIBCO BRL), either until control embryos reached Stage 10.5 (for RT-PCR), or until control embryos reached Stage 23/24 (for animal cap elongation photography). Staging of embryos was done according to Nieuwkoop and Faber, supra.

Total RNA was extracted from embryos and animal caps at Stage 10.5, and RT-PCR was performed as previously described (LaBonne and Whitman, Development 120: 463–472, 1994), using 20 amplification cycles for EF-1α and 25 for Xbra.

Results

Figure 8A:
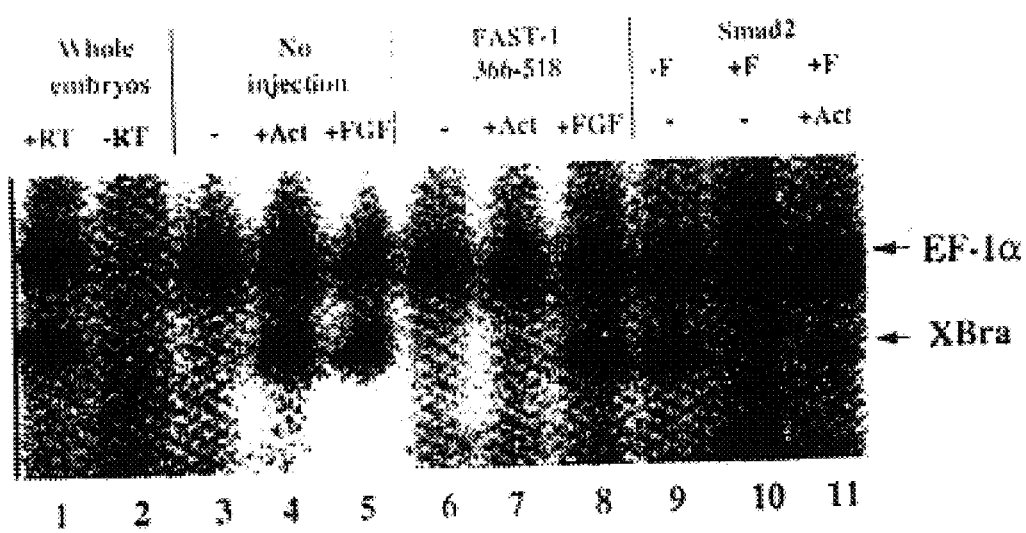
FIG. 8A shows an agarose gel containing RT-PCR amplification products that were generated using primers specific for the pan-mesodermal marker brachyury (Xbra), and the ubiquitously expressed marker EF1α, demonstrating that the FAST-1 SID inhibits activin-induced brachyury expression.

Animals caps from embryos expressing FAST-1 SID (FIG. 8A, lanes 6–8, 10, 11) in the absence (FIG. 8A, lanes 1–8) or presence (FIG. 8A, lanes 9–11) of overexpressed Smad2 were tested for the induction of the pan-mesodermal marker brachyury (Xbra). FIG. 8A shows an agarose gel containing electrophoretically resolved RT-PCR products from RNA extracted from animal caps cut at Stage 8–9, treated with activin or FGF, and harvested for RNA at Stage 10.5. The ubiquitously-expressed marker EF1α was also RT-PCR-amplified within each reaction, as an internal control for quantitation of brachyury PCR products. The symbols "+F" and "−F" denote samples from embryos that were injected with Smad2 mRNA plus or minus mRNA encoding the FAST-1 SID (FAST-1 aa366–518).

Activin-dependent induction of brachyury was inhibited by overexpressed FAST-1 SID. Moreover, inhibition was specific for the activin/TGF-β signalling pathway, since induction of brachyury by bFGF was unaffected by the FAST-1 SID (FIG. 8A). Activin-dependent induction of the endo-mesodermal marker Mix.1 also was inhibited by the FAST-1 SID, as was induction of mesodermal markers by Smad2. However, overexpression of Smad2 partially restored activin-dependent gene expression in the presence of the FAST-1 SID. These observations suggest that inhibition of mesoderm-specific gene expression is due to the sequestration of Smads by the FAST-1 SID.

Figure 8B:
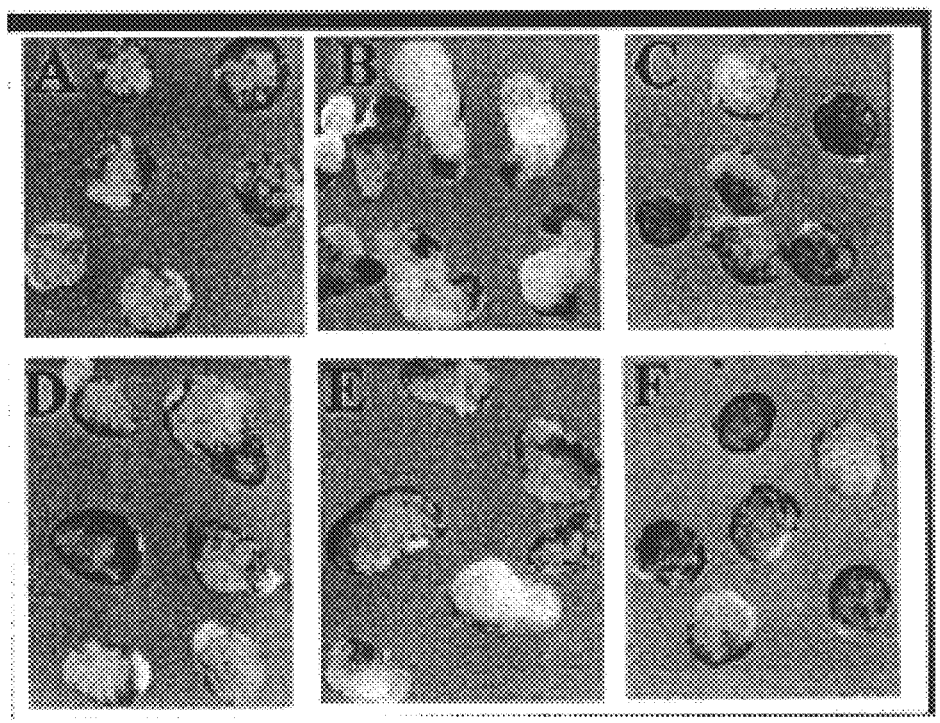
FIG. 8B (Panels A–F) shows a series of photographs of animal caps from control and experimentally-manipulated Xenopus embryos, demonstrating that the FAST-1 SID blocks activin induction of mesodermal cell movements in early embryos.

FIG. 8B shows a series of photographs of animal caps from control and experimentally-manipulated Xenopus embryos. Panel A shows unstimulated embryos; Panel B shows activin-stimulated embryos; Panel C shows activin-stimulated/FAST-1 SID-microinjected embryos; Panel D shows FGF-stimulated embryos; Panel E shows FGF-stimulated/FAST-1 SID-microinj ected embryos; and Panel F shows unstimulated/FAST-1 SID-microinjected embryos.

Activin-dependent elongation of animal caps, a marker of mesoderm induction, was inhibited by overexpressed FAST-1 SID (FIG. 8B, panel C). In contrast, like bFGF-induced brachyury expression, bFGF-dependent animal cap elongation was not inhibited by overexpressed FAST-1 SID (FIG. 8B, panels C and E). These results indicate that FAST-1 SID specifically inhibits the activin/TGF-β signalling pathway.

EXAMPLE X

Specific Binding of FAST-1 and Smad2 Domains in Vitro

The limitations of the yeast interaction trap method for monitoring protein-protein interactions (e.g., the difficulty of delivering compounds into yeast, and other non-specific effects due to yeast biology), made it desirable to develop an alternative method without such limitations. Hence, we developed an in vitro method to detect interactions between the FAST-1 Smad Interaction Domain (SID) and Smad2 MH2 domain. This method allows the detection of inhibitors of activin/TGFβ superfamily signalling.

Methods

The SID of FAST-1 was fused to a GST tag, expressed in *E. coli*, and isolated by binding to glutathione sepharose as described in an earlier section. As a control, GST was expressed and purified in parallel. Myc-tagged Smad1 or Smad2 MH2 domains were expressed in *Xenopus laevis* embryos by mRNA injection; Stage 9 embryos were lysed and assayed for MH2 domain expression level by Western blot analysis using anti-Myc antibodies (lane 1, uninjected; lane 2, injected with Myc-Smad1 MH2; lane 3, injected with Myc-Smad2 MH2). Lysates from Stage 9 embryos expressing Myc epitope-tagged Smad1 (lanes 4 and 6) or Smad2 MH2 (lanes 5 and 7) domains were also incubated with GST-control (lanes 4 and 5) or GST-FAST-1 SID (lanes 6 and 7) fusion protein. Protein complexes were precipitated by binding to glutathione-coated beads and precipitated proteins were resolved by Laemmli gel electrophoresis and subjected to Western blot analysis with anti-Myc antibodies.

Results

Figure 9:
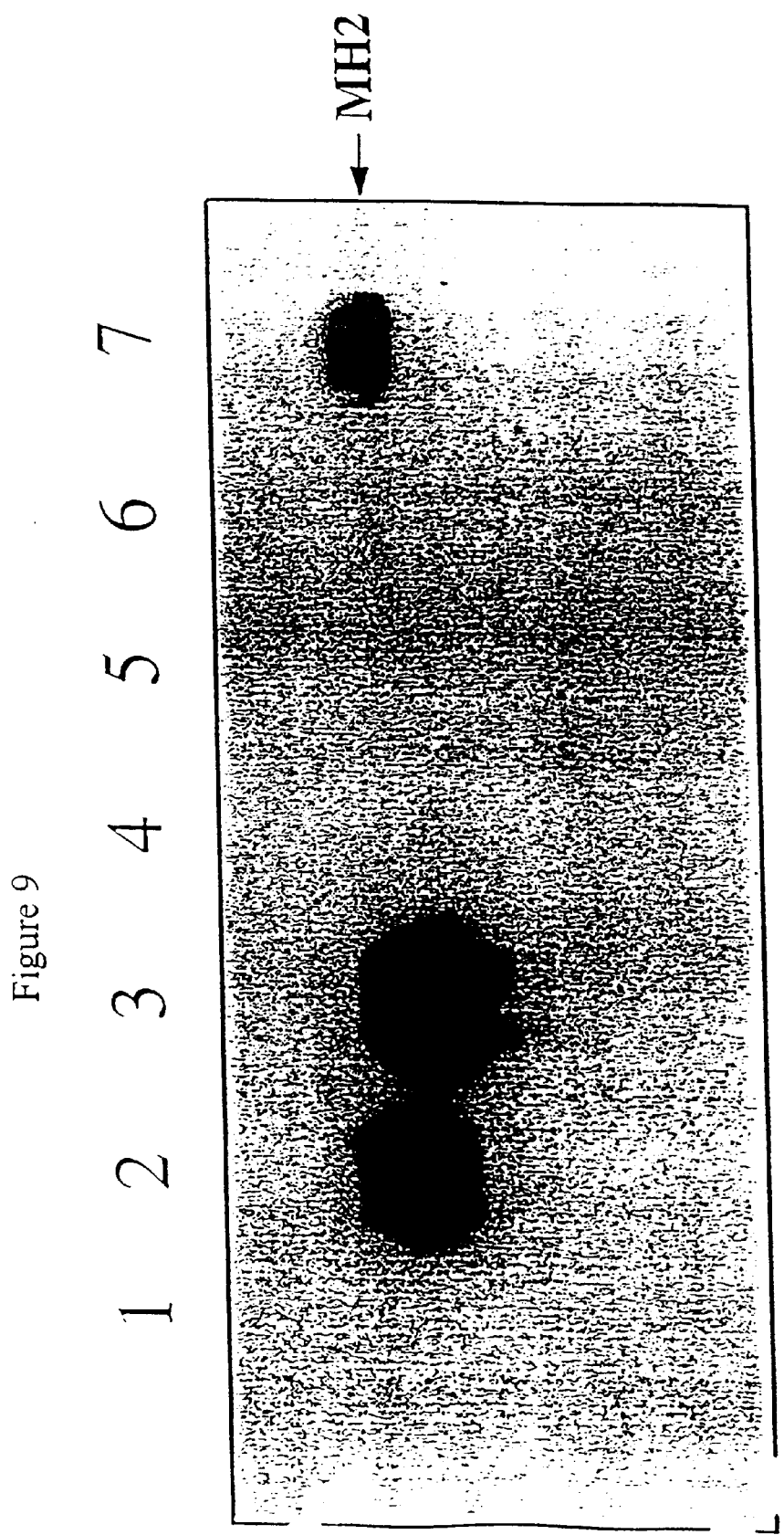
FIG. 9 shows a Western blot analysis, with anti-Myc antibody, of whole lysates and FAST-1 immunoprecipitates from lysates of control embryos and embryos expressing GST-tagged FAST-1 plus Myc-tagged Smad1 MH2 domain or Myc-tagged Smad2 MH2 domain, demonstrating that the Smad2 MH2 domain co-immunoprecipitates FAST-1 in an activin-stimulated manner.

FIG. 9 shows a Western blot analysis, using anti-Myc antibodies, of samples from uninjected embryos (lane 1), embryos expressing Myc-Smad1 MH2 domain (lanes 2, 4, 6,) and embryos expressing Myc-Smad2 MH2 domain (lanes 3, 5, 7). Lanes 1, 2, and 3 are whole lysates, lanes 4 and 5 are immunoprecipitates from lysates incubated with GST control protein, and lanes 6 and 7 are immunoprecipitates from lysates incubated with GST-FAST-1 SID. FIG. 9 shows that the FAST-1 SID specifically binds the Smad2 MH2 domain, but not the Smad1 MH2 domain (lane 7). That fact that these results, originally detected using the yeast interaction trap assay described in Example VII, may also be observed in our in vitro assay, confirms the validity of this approach for monitoring specific FAST-1/Smad2 interactions.

EXAMPLE XI

Identification of Human and Mouse Homologues of FAST-1

Since TGF-β superfamily signalling affects the development of a wide variety of organisms, we isolated cDNAs encoding mammalian homologues of Xenopus FAST-1.

We searched publicly available sequence databases for sequences with identity to the amino acid sequence of full length Xenopus FAST-1 (Chen et al., supra), and for sequences with identity to amino acids 380 to 506 of FAST-1 (corresponding to the FAST-1 SID).

Our search for sequences with identity to full length FAST-1 identified no candidate FAST-1 homologues. However, by using the amino acid sequences corresponding to the FAST-1 SID as a probe to screen sequence listing databases, we identified one sequence in the TIGR Human Gene Index (TIGR clone ID No. 64997; clones in the TIGR index are commercially available) with identity to the FAST-1 SID. The Genbank accession number of the human FAST-1 SID partial sequence is AA218611.

The human FAST1 SID clone had an insert size of approximately 300 base pairs, corresponding to a 100 amino acid long polypeptide. A cDNA clone encoding full-length human FAST-1 was isolated by screening a human cDNA library, by standard techniques, using the fragment encoding the human FAST-1 SID as a probe.

Degenerate primers were designed that correspond to regions conserved between human and Xenopus FAST-1. The primers were used in PCR reactions that contained cDNA from mouse embryonic stem cells as a template. A partial cDNA encoding mouse FAST-1 was obtained, which was used to screen mouse cDNA and genomic libraries to obtain the full-length mouse FAST-1 sequence.

EXAMPLE XII

FAST-1-Like Activity by the Human FAST-1 Homologue

We tested the candidate human homologue of FAST-1 for the ability to co-immunoprecipitate with Smad2.

Methods

The 300 base pair insert encoding the human FAST-1 SID was tagged with the Myc epitope by subcloning the insert into the pCS2(+)MT vector.

Myc-tagged human FAST-1 was co-expressed with GST-tagged Smad2 in Xenopus embryos in the presence or absence of activin stimulation. The microinjected embryos were then lysed and immunoprecipitated with anti-GST antibody, followed by bloating with anti-Myc antibody, as described in Example IV.

Results

The human Myc-tagged FAST-1 SID co-immunoprecipitates with GST-tagged Smad2, indicating that human FAST-1, like Xenopus FAST-1, is able to associate with Smad2. Also like Xenopus FAST-1, the human FAST-1 SID co-immuno-precipitates Smad4 in an activin-dependent-manner.

An amino acid sequence alignment of human, mouse, and Xenopus FAST-1 is shown in FIGS. 10A and 10B. Regions of FAST-1 polypeptides having identical amino acids are boxed. The human and mouse FAST-1 SIDs are comprised, at maximum, of human FAST-1 amino acids 234–365, and mouse FAST-1 amino acids 309–398.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

What is claimed is:

1. A substantially pure protein selected from the group consisting of SEQ ID NOs: 14, 15, 17, and 18, wherein said substantially pure protein is capable of binding a polypeptide selected from the group consisting of SEQ ID NOs: 2 and 5, and wherein said substantially pure protein is greater than 60% pure by weight.

2. A substantially pure polypeptide fragment of SEQ ID NO: 12, wherein said substantially pure polypeptide fragment is capable of binding a polypeptide selected from the group consisting of SEQ ID NO: 2 and 5, and wherein said substantially pure polypeptide fragment is greater than 60% pure by weight.

3. A substantially pure polypeptide encoded by a nucleic acid selected from the group consisting of SEQ ID NOS: 10 and 16, wherein said substantially pure polypeptide is capable of binding a polypeptide selected from the group consisting of SEQ ID NOs: 2 and 5, and wherein said substantially pure polypeptide is greater than 60% pure by weight.

* * * * *

UNITED STATES PATENT AND TRADEMARK OFFICE
CERTIFICATE OF CORRECTION

| | |
|---|---|
| PATENT NO. | : 6,365,711 B1 |
| APPLICATION NO. | : 09/087134 |
| DATED | : April 2, 2002 |
| INVENTOR(S) | : Malcolm Whitman et al. |

It is certified that error appears in the above-identified patent and that said Letters Patent is hereby corrected as shown below:

In the Specification

Column 1, Line number 11, please delete the paragraph beginning with "This invention" and ending with "the invention" and replace it with the following paragraph:
This invention was made with government support under HD024926, and HD029468 awarded by the National Institutes of Health. The government has certain rights in the invention.

Signed and Sealed this
Thirty-first Day of December, 2024

Derrick Brent
*Acting Director of the United States Patent and Trademark Office*

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 1658 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Other
      (B) LOCATION: 1...1
      (D) OTHER INFORMATION: Xenopus Smad2 coding region (xi) SEQUENCE DESCRIPTION: SEQ ID NO:1:

```
ATGTCGTCCA TCTTGCCTTT CACCCCGCCA GTAGTGAAGC GCCTGCTAGG ATGGAAGAAG      60

TCTGCAAGTG GCACCACAGG AGCAGGTGGC GATGAGCAGA ACGGACAGGA AGAGAAGTGG     120

TGCGAAAAAG CGGTAAAGAG CTTGGTGAAA AAACTGAAGA AAACGGGACA ATTAGACGAG     180

CTTGAGAAGG CGATCACGAC GCAGAACTGC AACACGAAAT GCGTAACGAT ACCAAGCACT     240

TGCTCTGAAA TTTGGGGACT GAGTACAGCA AATACCATAG ATCAGTGGGA TACCACAGGC     300

CTTTACAGCT TCTCTGAACA AACCAGGTCT CTTGATGGTC GACTCCAGGT GTCTCACCGT     360

AAAGGATTGC CGCATGTTAT CTACTGCAGA CTGTGGCGCT GGCCAGACCT GCACAGTCAT     420

CATGAACTGA AAGCAATCGA AAATTGTGAA TATGCTTTTA ACCTTAAAAA AGATGAAGTT     480

TGTGTCAATC CATACCATTA TCAGAGGGTG GAGACACCAG TTTTACCACC TGTATTAGTT     540

CCACGGCACA CGGAAATCTT GACAGAGCTG CCACCTCTTG ATGACTACAC GCATTCCATT     600

CCAGAAAACA CTAATTTTCC TGCAGGGATT GAACCTCAGA GCAATTATAT TCCAGAAACA     660

CCACCTCCTG GATATATTAG TGAAGATGGA GAAACTAGCG ATCAGCAACT TAACCAAAGC     720

ATGGACACAG GGTCACCAGC TGAGCTGTCT CCGAGTACAC TTTCTCCAGT CAACCACAAT     780

CTCGATTTGC AACCTGTCAC CTATTCGGAA CCTGCTTTTT GGTGCTCTAT AGCATACTAC     840

GAACTGAATC AGCGAGTAGG AGAAACTTTC CATGCATCGC AACCATCGCT TACCGTGGAC     900

GGCTTTACGG ACCCCTCAAA CTCTGAAAGG TTCTGCTTAG GTTTACTCTC AAATGTGAAC     960
```

-continued

```
CGAAATGCCA CGGTGGAAAT GACCAGGCGT CACATAGGAA GGGGTGTCCG GCTATATTAC    1020

ATCGGTGGAG AGGTGTTTGC AGAGTGCCTA AGTGATAGTG CTATTTTTGT TCAGAGTCCA    1080

AACTGTAACC AGCGATATGG ATGGCATCCA GCAACTGTAT GTAAGATTCC TCCAGGATGC    1140

AATCTGAAGA TTTTCAATAA TCAAGAGTTT GCGGCTCTCC TCGCTCAGTC TGTGAATCAA    1200

GGCTTTGAAG CAGTTTATCA GTTAACTCGA ATGTGCACCA TAAGGATGAG CTTTGTAAAA    1260

GGCTGGGGTG CTGAATACAG GCGACAGACC GTTACAAGCA CTCCATGCTG GATTGAGCTT    1320

CACCTGAATG GACCTTTGCA GTGGTTGGAC AAAGTGTTGA CACAGATGGG ATCCCCTTCA    1380

GTCCGCTGCT CAAGCATGTC CTAATGGTCT CCTCTTTTTA ATGTATTACC TGCGGGCGGC    1440

AACTGCAGTC CCAGCAACAG ACTCAATACA GCTTGTCTGT CGTAGTATTT GTGTGTGGTG    1500

CCCATGAACT GTTTACAATC CAAAAGAGAG AGAATAAAAA AGCAAAAACA GCACTTGAGA    1560

TCCCATCAAC GAAAAGCACC TTGTTGGATG ATGTTTCTGA TACTCTTAAA GTAGATCCGT    1620

GTATAAATGA CTCCTTACCT GGGAAAAGGG ACTTTTTC                           1658
```

(2) INFORMATION FOR SEQ ID NO:2:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Xenopus Smad2

(xi) SEQUENCE DESCRIPTION: SEQ ID NO:2:

```
Met Ser Ser Ile Leu Pro Phe Thr Pro Pro Val Val Lys Arg Leu Leu
 1               5                  10                  15

Gly Trp Lys Lys Ser Ala Ser Gly Thr Thr Gly Ala Gly Gly Asp Glu
            20                  25                  30

Gln Asn Gly Gln Glu Glu Lys Trp Cys Glu Lys Ala Val Lys Ser Leu
        35                  40                  45

Val Lys Lys Leu Lys Lys Thr Gly Gln Leu Asp Glu Leu Glu Lys Ala
 50                  55                  60

Ile Thr Thr Gln Asn Cys Asn Lys Cys Val Thr Ile Pro Ser Thr Thr
 65                  70                  75                  80

Cys Ser Glu Ile Trp Gly Leu Ser Thr Ala Asn Thr Ile Asp Gln Trp
                85                  90                  95

Asp Thr Thr Gly Leu Tyr Ser Phe Ser Glu Gln Thr Arg Ser Leu Asp
            100                 105                 110

Gly Arg Leu Gln Val Ser His Arg Lys Gly Leu Pro His Val Ile Tyr
        115                 120                 125

Cys Arg Leu Trp Arg Trp Pro Asp Leu His Ser His His Glu Leu Lys
130                 135                 140

Ala Ile Glu Asn Cys Glu Tyr Ala Phe Asn Leu Lys Lys Asp Glu Val
145                 150                 155                 160

Cys Val Asn Pro Tyr His Tyr Gln Arg Val Glu Thr Pro Val Leu Pro
                165                 170                 175

Pro Val Leu Val Pro Arg His Thr Glu Ile Leu Thr Glu Leu Pro Pro
            180                 185                 190
```

-continued

```
Leu Asp Asp Tyr Thr His Ser Ile Pro Glu Asn Thr Asn Phe Pro Ala
            195                 200                 205

Gly Ile Glu Pro Gln Ser Asn Tyr Ile Pro Glu Thr Pro Pro Pro Gly
            210                 215                 220

Tyr Ile Ser Glu Asp Gly Glu Thr Ser Asp Gln Gln Leu Asn Gln Ser
225                 230                 235                 240

Met Asp Thr Gly Ser Pro Ala Glu Leu Ser Pro Ser Thr Leu Ser Pro
            245                 250                 255

Val Asn His Asn Leu Asp Leu Gln Pro Val Thr Tyr Ser Glu Pro Ala
            260                 265                 270

Phe Trp Cys Ser Ile Ala Tyr Tyr Glu Leu Asn Gln Arg Val Gly Glu
            275                 280                 285

Thr Phe His Ala Ser Gln Pro Ser Leu Thr Val Asp Gly Phe Thr Asp
            290                 295                 300

Pro Ser Asn Ser Glu Arg Phe Cys Leu Gly Leu Leu Ser Asn Val Asn
305                 310                 315                 320

Arg Asn Ala Thr Val Glu Met Thr Arg Arg His Ile Gly Arg Gly Val
            325                 330                 335

Arg Leu Tyr Tyr Ile Gly Gly Glu Val Phe Ala Glu Cys Leu Ser Asp
            340                 345                 350

Ser Ala Ile Phe Val Gln Ser Pro Asn Cys Asn Gln Arg Tyr Gly Trp
            355                 360                 365

His Pro Ala Thr Val Cys Lys Ile Pro Pro Gly Cys Asn Leu Lys Ile
            370                 375                 380

Phe Asn Asn Gln Glu Phe Ala Ala Leu Leu Ala Gln Ser Val Asn Gln
385                 390                 395                 400

Gly Phe Glu Ala Val Tyr Gln Leu Thr Arg Met Cys Thr Ile Arg Met
            405                 410                 415

Ser Phe Val Lys Gly Trp Gly Ala Glu Tyr Arg Arg Gln Thr Val Thr
            420                 425                 430

Ser Thr Pro Cys Trp Ile Glu Leu His Leu Asn Gly Pro Leu Gln Trp
            435                 440                 445

Leu Asp Lys Val Leu Thr Gln Met Gly Ser Pro Ser Val Arg Cys Ser
450                 455                 460

Ser Met Ser
465
```

(2) INFORMATION FOR SEQ ID NO:3:

(i) SEQUENCE CHARACTERISTICS:
        (A) LENGTH: 194 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Xenopus Smad2 MH2 domain (xi) SEQUENCE DESCRIPTION: SEQ ID NO:3:

```
Trp Cys Ser Ile Ala Tyr Tyr Glu Leu Asn Gln Arg Val Gly Glu Thr
1               5                   10                  15

Phe His Ala Ser Gln Pro Ser Leu Thr Val Asp Gly Phe Thr Asp Pro
            20                  25                  30

Ser Asn Ser Glu Arg Phe Cys Leu Gly Leu Leu Ser Asn Val Asn Arg
```

```
            35                  40                  45
Asn Ala Thr Val Glu Met Thr Arg Arg His Ile Gly Arg Gly Val Arg
         50                  55                  60

Leu Tyr Tyr Ile Gly Gly Glu Val Phe Ala Glu Cys Leu Ser Asp Ser
65                  70                  75                  80

Ala Ile Phe Val Gln Ser Pro Asn Cys Asn Gln Arg Tyr Gly Trp His
                 85                  90                  95

Pro Ala Thr Val Cys Lys Ile Pro Pro Gly Cys Asn Leu Lys Ile Phe
                100                 105                 110

Asn Asn Gln Glu Phe Ala Ala Leu Leu Ala Gln Ser Val Asn Gln Gly
            115                 120                 125

Phe Glu Ala Val Tyr Gln Leu Thr Arg Met Cys Thr Ile Arg Met Ser
        130                 135                 140

Phe Val Lys Gly Trp Gly Ala Glu Tyr Arg Arg Gln Thr Val Thr Ser
145                 150                 155                 160

Thr Pro Cys Trp Ile Glu Leu His Leu Asn Gly Pro Leu Gln Trp Leu
                165                 170                 175

Asp Lys Val Leu Thr Gln Met Gly Ser Pro Ser Val Arg Cys Ser Ser
            180                 185                 190

Met Ser (2) INFORMATION FOR SEQ ID NO:4:

(i) SEQUENCE CHARACTERISTICS:
        (A) LENGTH: 1401 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Other
        (B) LOCATION: 1...1
        (D) OTHER INFORMATION: Human Smad2 coding region (xi) SEQUENCE DESCRIPTION: SEQ ID NO:4:

ATGTCGTCCA TCTTGCCATT CACGCCGCCA GTTGTGAAGA GACTGCTGGG ATGGAAGAAG      60

TCAGCTGGTG GGTCTGGAGG AGCAGGCGGA GGAGAGCAGA ATGGGCAGGA AGAAAAGTGG    120

TGTGAGAAAG CAGTGAAAAG TCTGGTGAAG AAGCTAAAGA AAACAGGACG ATTAGATGAG    180

CTTGAGAAAG CCATCACCAC TCAAAACTGT AATACTAAAT GTGTTACCAT ACCAAGCACT    240

TGCTCTGAAA TTTGGGGACT GAGTACACCA AATACGATAG ATCAGTGGGA TACAACAGGC    300

CTTTACAGCT TCTCTGAACA AACCAGGTCT CTTGATGGTC GTCTCCAGGT ATCCCATCGA    360

AAAGGATTGC CACATGTTAT ATATTGCCGA TTATGGCGCT GGCCTGATCT TCACAGTCAT    420

CATGAACTCA AGGCAATTGA AAACTGCGAA TATGCTTTTA ATCTTAAAAA GGATGAAGTA    480

TGTGTAAACC CTTACCACTA TCAGAGAGTT GAGACACCAG TTTTGCCTCC AGTATTAGTG    540

CCCCGACACA CCGAGATCCT AACAGAACTT CCGCCTCTGG ATGACTATAC TCACTCCATT    600

CCAGAAAACA CTAACTTCCC AGCAGGAATT GAGCCACAGA GTAATTATAT TCCAGAAACG    660

CCACCTCCTG GATATATCAG TGAAGATGGA GAAACAAGTG ACCAACAGTT GAATCAAAGT    720

ATGGACACAG GCTCTCCAGC AGAACTATCT CCTACTACTC TTTCCCCTGT TAATCATAGC    780

TTGGATTTAC AGCCAGTTAC TTACTCAGAA CCTGCATTTT GGTGTTCAAT AGCATATATT    840

GAATTAAATC AGAGGGTTGG AGAAACCTTC CATGCATCAC AGCCCTCACT CACTGTAGAT    900
```

```
GGCTTTACAG ACCCATCAAA TTCAGAGAGG TTCTGCTTAG GTTACTCTC CAATGTTAAC      960

CGAAATGCCA CGGTAGAAAT GACAAGAAGG CATATAGGAA GAGGAGTGCG CTTATACTAC    1020

ATAGGTGGGG AAGTTTTTGC TGAGTGCCTA AGTGATAGTG CAATCTTTGT GCAGAGCCCC    1080

AATTGTAATC AGAGATATGG CTGGCACCCT GCAACAGTGT GTAAAATTCC ACCAGGCTGT    1140

AATCTGAAGA TCTTCAACAA CCAGGAATTT GCTGCTCTTC TGGCTCAGTC TGTTAATCAG    1200

GGTTTTGAAG CCGTCTATCA GCTAACTAGA ATGTGCACCA TAAGAATGAG TTTTGTGAAA    1260

GGGTGGGGAG CAGAATACCG AAGGCAGACG GTAACAAGTA CTCCTTGCTG GATTGAACTT    1320

CATCTGAATG GACCTCTACA GTGGTTGGAC AAAGTATTAA CTCAGATGGG ATCCCCTTCA    1380

GTGCGTTGCT CAAGCATGTC A                                             1401

(2) INFORMATION FOR SEQ ID NO:5:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Human Smad2

(xi) SEQUENCE DESCRIPTION: SEQ ID NO:5:

Met Ser Ser Ile Leu Pro Phe Thr Pro Pro Val Val Lys Arg Leu Leu
 1               5                  10                  15

Gly Trp Lys Lys Ser Ala Gly Gly Ser Gly Gly Ala Gly Gly Gly Glu
                20                  25                  30

Gln Asn Gly Gln Glu Glu Lys Trp Cys Glu Lys Ala Val Lys Ser Leu
            35                  40                  45

Val Lys Lys Leu Lys Lys Thr Gly Arg Leu Asp Glu Leu Glu Lys Ala
        50                  55                  60

Ile Thr Thr Gln Asn Cys Asn Thr Lys Cys Val Thr Ile Pro Ser Thr
65                  70                  75                  80

Cys Ser Glu Ile Trp Gly Leu Ser Thr Pro Asn Thr Ile Asp Gln Trp
                85                  90                  95

Asp Thr Thr Gly Leu Tyr Ser Phe Ser Glu Gln Thr Arg Ser Leu Asp
            100                 105                 110

Gly Arg Leu Gln Val Ser His Arg Lys Gly Leu Pro His Val Ile Tyr
        115                 120                 125

Cys Arg Leu Trp Arg Trp Pro Asp Leu His Ser His His Glu Leu Lys
    130                 135                 140

Ala Ile Glu Asn Cys Glu Tyr Ala Phe Asn Leu Lys Lys Asp Glu Val
145                 150                 155                 160

Cys Val Asn Pro Tyr His Tyr Gln Arg Val Glu Thr Pro Val Leu Pro
                165                 170                 175

Pro Val Leu Val Pro Arg His Thr Glu Ile Leu Thr Glu Leu Pro Pro
            180                 185                 190

Leu Asp Asp Tyr Thr His Ser Ile Pro Glu Asn Thr Asn Phe Pro Ala
        195                 200                 205

Gly Ile Glu Pro Gln Ser Asn Tyr Ile Pro Glu Thr Pro Pro Pro Gly
    210                 215                 220

Tyr Ile Ser Glu Asp Gly Glu Thr Ser Asp Gln Gln Leu Asn Gln Ser
```

-continued

```
225                 230                 235                 240
Met Asp Thr Gly Ser Pro Ala Glu Leu Ser Pro Thr Thr Leu Ser Pro
                245                 250                 255

Val Asn His Ser Leu Asp Leu Gln Pro Val Thr Tyr Ser Glu Pro Ala
                260                 265                 270

Phe Trp Cys Ser Ile Ala Tyr Tyr Glu Leu Asn Gln Arg Val Gly Glu
            275                 280                 285

Thr Phe His Ala Ser Gln Pro Ser Leu Thr Val Asp Gly Phe Thr Asp
        290                 295                 300

Pro Ser Asn Ser Glu Arg Phe Cys Leu Gly Leu Leu Ser Asn Val Asn
305                 310                 315                 320

Arg Asn Ala Thr Val Glu Met Thr Arg Arg His Ile Gly Arg Gly Val
                325                 330                 335

Arg Leu Tyr Tyr Ile Gly Gly Glu Val Phe Ala Glu Cys Leu Ser Asp
                340                 345                 350

Ser Ala Ile Phe Val Gln Ser Pro Asn Cys Asn Gln Arg Tyr Gly Trp
                355                 360                 365

His Pro Ala Thr Val Cys Lys Ile Pro Pro Gly Cys Asn Leu Lys Ile
        370                 375                 380

Phe Asn Asn Gln Glu Phe Ala Ala Leu Leu Ala Gln Ser Val Asn Gln
385                 390                 395                 400

Gly Phe Glu Ala Val Tyr Gln Leu Thr Arg Met Cys Thr Ile Arg Met
                405                 410                 415

Ser Phe Val Lys Gly Trp Gly Ala Glu Tyr Arg Arg Gln Thr Val Thr
                420                 425                 430

Ser Thr Pro Cys Trp Ile Glu Leu His Leu Asn Gly Pro Leu Gln Trp
            435                 440                 445

Leu Asp Lys Val Leu Thr Gln Met Gly Ser Pro Ser Val Arg Cys Ser
450                 455                 460

Ser Met Ser
465

(2) INFORMATION FOR SEQ ID NO:6:

(i) SEQUENCE CHARACTERISTICS:
        (A) LENGTH: 194 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Human Smad2 MH2 domain (xi) SEQUENCE DESCRIPTION: SEQ ID NO:6:

Trp Cys Ser Ile Ala Tyr Tyr Glu Leu Asn Gln Arg Val Gly Glu Thr
1               5                   10                  15

Phe His Ala Ser Gln Pro Ser Leu Thr Val Asp Gly Phe Thr Asp Pro
            20                  25                  30

Ser Asn Ser Glu Arg Phe Cys Leu Gly Leu Leu Ser Asn Val Asn Arg
        35                  40                  45

Asn Ala Thr Val Glu Met Thr Arg Arg His Ile Gly Arg Gly Val Arg
    50                  55                  60

Leu Tyr Tyr Ile Gly Gly Glu Val Phe Ala Glu Cys Leu Ser Asp Ser
65                  70                  75                  80
```

-continued

```
Ala Ile Phe Val Gln Ser Pro Asn Cys Asn Gln Arg Tyr Gly Trp His
                85                  90                  95

Pro Ala Thr Val Cys Lys Ile Pro Pro Gly Cys Asn Leu Lys Ile Phe
            100                 105                 110

Asn Asn Gln Glu Phe Ala Ala Leu Leu Ala Gln Ser Val Asn Gln Gly
        115                 120                 125

Phe Glu Ala Val Tyr Gln Leu Thr Arg Met Cys Thr Ile Arg Met Ser
    130                 135                 140

Phe Val Lys Gly Trp Gly Ala Glu Tyr Arg Arg Gln Thr Val Thr Ser
145                 150                 155                 160

Thr Pro Cys Trp Ile Glu Leu His Leu Asn Gly Pro Leu Gln Trp Leu
                165                 170                 175

Asp Lys Val Leu Thr Gln Met Gly Ser Pro Ser Val Arg Cys Ser Ser
            180                 185                 190

Met Ser (2) INFORMATION FOR SEQ ID NO:7:

(i) SEQUENCE CHARACTERISTICS:
        (A) LENGTH: 2234 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1272
        (D) OTHER INFORMATION:
        (A) NAME/KEY: Other
        (B) LOCATION: 1...1
        (D) OTHER INFORMATION: Human Smad3 coding region (xi) SEQUENCE DESCRIPTION: SEQ ID NO:7:

ATG TCG TCC ATC CTG CCT TTC ACT CCC CCG ATC GTG AAG CGC CTG CTG        48
Met Ser Ser Ile Leu Pro Phe Thr Pro Pro Ile Val Lys Arg Leu Leu
 1               5                  10                  15

GGC TGG AAG AAG GGC GAG CAG AAC GGG CAG GAG GAG AAA TGG TGC GAG        96
Gly Trp Lys Lys Gly Glu Gln Asn Gly Gln Glu Glu Lys Trp Cys Glu
                20                  25                  30

AAG GCG GTC AAG AGC CTG GTC AAG AAA CTC AAG AAG ACG GGG CAG CTG       144
Lys Ala Val Lys Ser Leu Val Lys Lys Leu Lys Lys Thr Gly Gln Leu
            35                  40                  45

GAC GAG CTG GAG AAG GCC ATC ACC ACG CAG AAC GTC AAC ACC AAG TGC       192
Asp Glu Leu Glu Lys Ala Ile Thr Thr Gln Asn Val Asn Thr Lys Cys
        50                  55                  60

ATC ACC ATC CCC AGG TCC CTG GAT GGC CGG TTG CAG GTG TCC CAT CGG       240
Ile Thr Ile Pro Arg Ser Leu Asp Gly Arg Leu Gln Val Ser His Arg
65                  70                  75                  80

AAG GGG CTC CCT CAT GTC ATC TAC TGC CCT GTG CGA TGG CCA GAC CTG       288
Lys Gly Leu Pro His Val Ile Tyr Cys Pro Val Arg Trp Pro Asp Leu
                85                  90                  95

CAC AGC CAC CAC GAG CTG CGG GCC ATG GAG CTG TGT GAG TTC GCC TTC       336
His Ser His His Glu Leu Arg Ala Met Glu Leu Cys Glu Phe Ala Phe
                100                 105                 110

AAT ATG AAG AAG GAC GAG GTC TGC GTG AAT CCC TAC CAC TAC CAG AGA       384
Asn Met Lys Lys Asp Glu Val Cys Val Asn Pro Tyr His Tyr Gln Arg
        115                 120                 125

GTA GAG ACA CCA GTT CTA CCT CCT GTG TTG GTG CCA CGC CAC ACA GAG       432
Val Glu Thr Pro Val Leu Pro Pro Val Leu Val Pro Arg His Thr Glu
```

```
              130                 135                 140
ATC CCG GCC GAG TTC CCC CCA CTG GAC GAC TAC AGC CAT TCC ATC CCC         480
Ile Pro Ala Glu Phe Pro Pro Leu Asp Asp Tyr Ser His Ser Ile Pro
145                 150                 155                 160

GAA AAC ACT AAC TTC CCC GCA GGC ATC GAG CCC CAG AGC AAT ATT CCA         528
Glu Asn Thr Asn Phe Pro Ala Gly Ile Glu Pro Gln Ser Asn Ile Pro
                165                 170                 175

GAG ACC CCA CCC CCT GGC TAC CTG AGT GAA GAT GGA GAA ACC AGT GAC         576
Glu Thr Pro Pro Pro Gly Tyr Leu Ser Glu Asp Gly Glu Thr Ser Asp
            180                 185                 190

CAC CAG ATG AAC CAC AGC ATG GAC GCA GGT TCT CCA AAC CTA TCC CCG         624
His Gln Met Asn His Ser Met Asp Ala Gly Ser Pro Asn Leu Ser Pro
        195                 200                 205

AAT CCG ATG TCC CCA GCA CAT AAT AAC TTG GAC CTG CAG CCA GTT ACC         672
Asn Pro Met Ser Pro Ala His Asn Asn Leu Asp Leu Gln Pro Val Thr
    210                 215                 220

TAC TGC GAG CCG GCC TTC TGG TGC TCC ATC TCC TAC TAC GAG CTG AAC         720
Tyr Cys Glu Pro Ala Phe Trp Cys Ser Ile Ser Tyr Tyr Glu Leu Asn
225                 230                 235                 240

CAG CGC GTC GGG GAG ACA TTC CAC GCC TCG CAG CCA TCC ATG ACT GTG         768
Gln Arg Val Gly Glu Thr Phe His Ala Ser Gln Pro Ser Met Thr Val
                245                 250                 255

GAT GGC TTC ACC GAC CCC TCC AAT TCG GAG CGC TTC TGC CTA GGG CTG         816
Asp Gly Phe Thr Asp Pro Ser Asn Ser Glu Arg Phe Cys Leu Gly Leu
            260                 265                 270

CTC TCC AAT GTC AAC AGG AAT GCA GCA GTG GAG CTG ACA CGG AGA CAC         864
Leu Ser Asn Val Asn Arg Asn Ala Ala Val Glu Leu Thr Arg Arg His
        275                 280                 285

ATC GGA AGA GGC GTG CGG CTC TAC TAC ATC GGA GGG GAG GTC TTC GCA         912
Ile Gly Arg Gly Val Arg Leu Tyr Tyr Ile Gly Gly Glu Val Phe Ala
    290                 295                 300

GAG TGC CTC AGT GAC AGC GCT ATT TTT GTC CAG TCT CCC AAC TGT AAC         960
Glu Cys Leu Ser Asp Ser Ala Ile Phe Val Gln Ser Pro Asn Cys Asn
305                 310                 315                 320

CAG CGC TAT GGC TGG CAC CCG GCC ACC GTC TGC AAG ATC CCA CCA GGA        1008
Gln Arg Tyr Gly Trp His Pro Ala Thr Val Cys Lys Ile Pro Pro Gly
                325                 330                 335

TGC AAC CTG AAG ATC TTC AAC AAC CAG GAG TTC GCT GCC CTC CTG GCC        1056
Cys Asn Leu Lys Ile Phe Asn Asn Gln Glu Phe Ala Ala Leu Leu Ala
            340                 345                 350

CAG TCG GTC AAC CAG GGC TTT GAG GCT GTC TAC CAG TTG ACC CGA ATG        1104
Gln Ser Val Asn Gln Gly Phe Glu Ala Val Tyr Gln Leu Thr Arg Met
        355                 360                 365

TGC ACC ATC CGC ATG AGC TTC GTC AAA GGC TGG GGA GCG GAG TAC AGG        1152
Cys Thr Ile Arg Met Ser Phe Val Lys Gly Trp Gly Ala Glu Tyr Arg
    370                 375                 380

AGA CAG ACT GTG ACC AGT ACC CCC TGC TGG ATT GAG CTG CAC CTG AAT        1200
Arg Gln Thr Val Thr Ser Thr Pro Cys Trp Ile Glu Leu His Leu Asn
385                 390                 395                 400

GGG CCT TTG CAG TGG CTT GAC AAG GTC CTC ACC CAG ATG GGC TCC CCA        1248
Gly Pro Leu Gln Trp Leu Asp Lys Val Leu Thr Gln Met Gly Ser Pro
                405                 410                 415

AGC ATC CGC TGT TCC AGT GTG TCT TAGAGACATC AAGTATGGTA GGGGAGGGCA       1302
Ser Ile Arg Cys Ser Ser Val Ser
            420

GGCTTGGGGA AAATGGCCAT ACAGGAGGTG GAGAAAATTG GAACTCTACT CAACCCATTG      1362

TTGTCAAGGA AGAAGAAATC TTTCTCCCTC AACTGAAGGG GTGCACCCAC CTGTTTTCTG      1422

AAACACACGA GCAAACCCAG AGGTGGATGT TATGAACAGC TGTGTCTGCC AAACACATTT      1482
```

-continued

```
ACCCTTTGGC CCCACTTTGA AGGGCAAGAA ATGGCGTCTG CTCTGGTGGC TTAAGTGAGC      1542

AGAACAGGTA GTATTACACC ACCGGCACCC TCCCCCCAGA CTCTTTTTTT GAGTGACAGC      1602

TTTCTGGGAT GTCACAGTCC AACCAGAAAC GCCCCTCTGT CTAGGACTGC AGTGTGGAGT      1662

TCACCTTGGA AGGGCGTTCT AGGTAGGAAG AGCCCGCACG ATGCAGACCT CATGCCCAGC      1722

TCTCTGACGC TTGTGACAGT GCCTCTTCCA GTGAACATTC CCAGCCCAGC CCCGCCCCGT      1782

TGTGAGCTGG ATAGACTTGG GATGGGGAGG GAGGGAGTTT TGTCTGTCTC CCTCCCCTCT      1842

CAGAACATAC TGATTGGGAG GTGCGTGTTC AGCAGAACCT GCACACAGGA CAGCGGGAAA      1902

AATCGATGAG CGCCACCTCT TTAAAAACTC ACTTACGTTG TCCTTTTTCA CTTTGAAAAG      1962

TTGGAAGGAC TGCTGAGGCC CAGTGCATAT GCAATGTATA GTGTCTATTA TCACATTAAT      2022

CTCAAAGAGA TTCGAATGAC GGTAAGTGTT CTCATGAAGC AGGAGGCCCT TGTCGTGGGA      2082

TGGCATTTGG TCTCAGGCAG CACCACACTG GGTGCGTCTC CAGTCATCTG TAAGAGCTTG      2142

CTCCAGATTC TGATGCATAC GGCTATATTG GTTTATGTAG TCAGTTGCAT TCATTAAATC      2202

AACTTTATCA TATGCTCAAA AAAAAAAAAA AG                                   2234
```

(2) INFORMATION FOR SEQ ID NO:8:

(i) SEQUENCE CHARACTERISTICS:
        (A) LENGTH: 424 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Human Smad3

(xi) SEQUENCE DESCRIPTION: SEQ ID NO:8:

```
Met Ser Ser Ile Leu Pro Phe Thr Pro Pro Ile Val Lys Arg Leu Leu
1               5                   10                  15

Gly Trp Lys Lys Gly Glu Gln Asn Gly Gln Glu Glu Lys Trp Cys Glu
            20                  25                  30

Lys Ala Val Lys Ser Leu Val Lys Lys Leu Lys Lys Thr Gly Gln Leu
        35                  40                  45

Asp Glu Leu Glu Lys Ala Ile Thr Thr Gln Asn Val Asn Thr Lys Cys
    50                  55                  60

Ile Thr Ile Pro Arg Ser Leu Asp Gly Arg Leu Gln Val Ser His Arg
65                  70                  75                  80

Lys Gly Leu Pro His Val Ile Tyr Cys Pro Val Arg Trp Pro Asp Leu
                85                  90                  95

His Ser His His Glu Leu Arg Ala Met Glu Leu Cys Glu Phe Ala Phe
            100                 105                 110

Asn Met Lys Lys Asp Glu Val Cys Val Asn Pro Tyr His Tyr Gln Arg
        115                 120                 125

Val Glu Thr Pro Val Leu Pro Pro Val Leu Val Pro Arg His Thr Glu
    130                 135                 140

Ile Pro Ala Glu Phe Pro Pro Leu Asp Asp Tyr Ser His Ser Ile Pro
145                 150                 155                 160

Glu Asn Thr Asn Phe Pro Ala Gly Ile Glu Pro Gln Ser Asn Ile Pro
                165                 170                 175

Glu Thr Pro Pro Pro Gly Tyr Leu Ser Glu Asp Gly Glu Thr Ser Asp
```

```
                    180             185             190
His Gln Met Asn His Ser Met Asp Ala Gly Ser Pro Asn Leu Ser Pro
            195             200             205

Asn Pro Met Ser Pro Ala His Asn Asn Leu Asp Leu Gln Pro Val Thr
210             215             220

Tyr Cys Glu Pro Ala Phe Trp Cys Ser Ile Ser Tyr Glu Leu Asn
225             230             235             240

Gln Arg Val Gly Glu Thr Phe His Ala Ser Gln Pro Ser Met Thr Val
            245             250             255

Asp Gly Phe Thr Asp Pro Ser Asn Ser Glu Arg Phe Cys Leu Gly Leu
            260             265             270

Leu Ser Asn Val Asn Arg Asn Ala Ala Val Glu Leu Thr Arg Arg His
            275             280             285

Ile Gly Arg Gly Val Arg Leu Tyr Tyr Ile Gly Gly Glu Val Phe Ala
            290             295             300

Glu Cys Leu Ser Asp Ser Ala Ile Phe Val Gln Ser Pro Asn Cys Asn
305             310             315             320

Gln Arg Tyr Gly Trp His Pro Ala Thr Val Cys Lys Ile Pro Pro Gly
            325             330             335

Cys Asn Leu Lys Ile Phe Asn Asn Gln Glu Phe Ala Ala Leu Leu Ala
            340             345             350

Gln Ser Val Asn Gln Gly Phe Glu Ala Val Tyr Gln Leu Thr Arg Met
            355             360             365

Cys Thr Ile Arg Met Ser Phe Val Lys Gly Trp Gly Ala Glu Tyr Arg
            370             375             380

Arg Gln Thr Val Thr Ser Thr Pro Cys Trp Ile Glu Leu His Leu Asn
385             390             395             400

Gly Pro Leu Gln Trp Leu Asp Lys Val Leu Thr Gln Met Gly Ser Pro
            405             410             415

Ser Ile Arg Cys Ser Ser Val Ser
            420

(2) INFORMATION FOR SEQ ID NO:9:

(i) SEQUENCE CHARACTERISTICS:
        (A) LENGTH: 194 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Human Smad3 MH2 domain (xi) SEQUENCE DESCRIPTION: SEQ ID NO:9:

Trp Cys Ser Ile Ser Tyr Tyr Glu Leu Asn Gln Arg Val Gly Glu Thr
1               5               10              15

Phe His Ala Ser Gln Pro Ser Met Thr Val Asp Gly Phe Thr Asp Pro
            20              25              30

Ser Asn Ser Glu Arg Phe Cys Leu Gly Leu Leu Ser Asn Val Asn Arg
            35              40              45

Asn Ala Ala Val Glu Leu Thr Arg Arg His Ile Gly Arg Gly Val Arg
            50              55              60

Leu Tyr Tyr Ile Gly Gly Glu Val Phe Ala Glu Cys Leu Ser Asp Ser
65              70              75              80
```

```
Ala Ile Phe Val Gln Ser Pro Asn Cys Asn Gln Arg Tyr Gly Trp His
              85                  90                  95

Pro Ala Thr Val Cys Lys Ile Pro Pro Gly Cys Asn Leu Lys Ile Phe
             100                 105                 110

Asn Asn Gln Glu Phe Ala Ala Leu Leu Ala Gln Ser Val Asn Gln Gly
         115                 120                 125

Phe Glu Ala Val Tyr Gln Leu Thr Arg Met Cys Thr Ile Arg Met Ser
     130                 135                 140

Phe Val Lys Gly Trp Gly Ala Glu Tyr Arg Arg Gln Thr Val Thr Ser
145                 150                 155                 160

Thr Pro Cys Trp Ile Glu Leu His Leu Asn Gly Pro Leu Gln Trp Leu
                 165                 170                 175

Asp Lys Val Leu Thr Gln Met Gly Ser Pro Ser Ile Arg Cys Ser Ser
             180                 185                 190

Val Ser (2) INFORMATION FOR SEQ ID NO:10:

(i) SEQUENCE CHARACTERISTICS:
        (A) LENGTH: 1605 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1554
        (D) OTHER INFORMATION:
        (A) NAME/KEY: Other
        (B) LOCATION: 1...1
        (D) OTHER INFORMATION: Xenopus FAST-1 coding region (xi) SEQUENCE DESCRIPTION: SEQ ID NO:10:

ATG AGA GAC CCC TCC AGT CTG TAC TCA GGA TTC CCA GCT GGA TCC CAG        48
Met Arg Asp Pro Ser Ser Leu Tyr Ser Gly Phe Pro Ala Gly Ser Gln
 1               5                  10                  15

TAT GAA AGT GTG GAG CCT CCC AGC CTT GCC CTG CTG AGC TCT ATA GAC        96
Tyr Glu Ser Val Glu Pro Pro Ser Leu Ala Leu Leu Ser Ser Ile Asp
             20                  25                  30

CAG GAG CAG CTC CCA GTG GCC ACC GGC CAG TCC TAT AAT CAC AGT GTC       144
Gln Glu Gln Leu Pro Val Ala Thr Gly Gln Ser Tyr Asn His Ser Val
         35                  40                  45

CAG CCT TGG CCC CAA CCT TGG CCA CCC TTG TCC CTG TAC AGA GAG GGG       192
Gln Pro Trp Pro Gln Pro Trp Pro Pro Leu Ser Leu Tyr Arg Glu Gly
     50                  55                  60

GGC ACG TGG AGC CCA GAC AGA GGC AGT ATG TAT GGA CTC TCC CCC GGC       240
Gly Thr Trp Ser Pro Asp Arg Gly Ser Met Tyr Gly Leu Ser Pro Gly
65                  70                  75                  80

ACC CAC GAG GGC TCC TGC ACC CAC ACT CAC GAG GGC CCC AAG GAC TCA       288
Thr His Glu Gly Ser Cys Thr His Thr His Glu Gly Pro Lys Asp Ser
                 85                  90                  95

ATG GCA GGA GAC CAG ACC AGG TCC AGG AAG AGC AAA AAG AAT TAT           336
Met Ala Gly Asp Gln Thr Arg Ser Arg Lys Ser Lys Lys Asn Tyr
             100                 105                 110

CAT CGA TAT AAC AAG CCC CCC TAT TCC TAC CTG GCT ATG ATT GCC CTG       384
His Arg Tyr Asn Lys Pro Pro Tyr Ser Tyr Leu Ala Met Ile Ala Leu
         115                 120                 125

GTC ATC CAG AAC TCG CCC GAG AAG AGG CTC AAA CTC TCC CAG ATC CTG       432
Val Ile Gln Asn Ser Pro Glu Lys Arg Leu Lys Leu Ser Gln Ile Leu
```

```
              130                 135                 140
AAG GAG GTC AGT ACA CTC TTC CCC TTC TTT AAT GGG GAT TAT ATG GGT        480
Lys Glu Val Ser Thr Leu Phe Pro Phe Phe Asn Gly Asp Tyr Met Gly
145                 150                 155                 160

TGG AAA GAC TCC ATC AGG CAC AAC TTG TCT TCC AGT GAC TGC TTT AAG        528
Trp Lys Asp Ser Ile Arg His Asn Leu Ser Ser Ser Asp Cys Phe Lys
                165                 170                 175

AAG ATT CTC AAA GAC CCT GGA AAG CCC CAG GCC AAG GGT AAC TTC TGG        576
Lys Ile Leu Lys Asp Pro Gly Lys Pro Gln Ala Lys Gly Asn Phe Trp
                    180                 185                 190

ACG GTG GAT GTT AGC CGG ATT CCT CTG GAT GCG ATG AAG CTG CAG AAC        624
Thr Val Asp Val Ser Arg Ile Pro Leu Asp Ala Met Lys Leu Gln Asn
                    195                 200                 205

ACT GCG TTG ACC CGA GGT GGA TCA GAC TAC TTT GTC CAG GAT TTG GCT        672
Thr Ala Leu Thr Arg Gly Gly Ser Asp Tyr Phe Val Gln Asp Leu Ala
210                 215                 220

CCA TAC ATC CTA CAT AAC TAT AAA TAT GAG CAC AAT GCA GGG GCG TAT        720
Pro Tyr Ile Leu His Asn Tyr Lys Tyr Glu His Asn Ala Gly Ala Tyr
225                 230                 235                 240

GGT CAC CAG ATG CCT CCA AGT CAT GCC AGA TCC CTG TCT TTG GCA GAG        768
Gly His Gln Met Pro Pro Ser His Ala Arg Ser Leu Ser Leu Ala Glu
                    245                 250                 255

GAC TCT CAA CAG ACC AAC ACT GGT GGC AAA CTT AAC ACA TCC TTT ATG        816
Asp Ser Gln Gln Thr Asn Thr Gly Gly Lys Leu Asn Thr Ser Phe Met
            260                 265                 270

ATT GAT TCC CTA CTC CAT GAC CTG CAA GAG GTG GAT CTG CCT GAT GCC        864
Ile Asp Ser Leu Leu His Asp Leu Gln Glu Val Asp Leu Pro Asp Ala
                275                 280                 285

TCC AGG AAC CTT GAG AAC CAA AGG ATC TCT CCG GCT GTA GCC ATG AAC        912
Ser Arg Asn Leu Glu Asn Gln Arg Ile Ser Pro Ala Val Ala Met Asn
290                 295                 300

AAT ATG TGG AGC TCT GCT CCT CTT CTC TAC ACT CAT TCC AAG CCA ACA        960
Asn Met Trp Ser Ser Ala Pro Leu Leu Tyr Thr His Ser Lys Pro Thr
305                 310                 315                 320

AGG AAT GCC AGA AGC CCT GGT TTG TCC ACC ATC CAT TCC ACG TAC TCC       1008
Arg Asn Ala Arg Ser Pro Gly Leu Ser Thr Ile His Ser Thr Tyr Ser
                325                 330                 335

TCT TCC AGC TCC AGC ATT TCT ACA ATC TCC CCC GTT GGG TTT CAG AAG       1056
Ser Ser Ser Ser Ser Ile Ser Thr Ile Ser Pro Val Gly Phe Gln Lys
                340                 345                 350

GAG CAG GAG AAA AGT GGT CGA CAA ACT CAA AGG GTT GGC CAT CCC ATT       1104
Glu Gln Glu Lys Ser Gly Arg Gln Thr Gln Arg Val Gly His Pro Ile
            355                 360                 365

AAA CGA TCA AGA GAG GAT GAT GAC TGC AGT ACC ACA TCT TCA GAT CCT       1152
Lys Arg Ser Arg Glu Asp Asp Asp Cys Ser Thr Thr Ser Ser Asp Pro
370                 375                 380

GAC ACT GGG AAC TAC TCT CCC ATT GAG CCC CCA AAG AAG ATG CCC TTG       1200
Asp Thr Gly Asn Tyr Ser Pro Ile Glu Pro Pro Lys Lys Met Pro Leu
385                 390                 395                 400

CTT TCA TTG GAC TTG CCC ACT TCT TAC ACA AAG AGT GTG GCA CCT AAT       1248
Leu Ser Leu Asp Leu Pro Thr Ser Tyr Thr Lys Ser Val Ala Pro Asn
                405                 410                 415

GTA GTG GCA CCA CCA AGT GTC CTG CCC TTC TTT CAT TTT CCT CGC TTC       1296
Val Val Ala Pro Pro Ser Val Leu Pro Phe Phe His Phe Pro Arg Phe
                420                 425                 430

ACC TAC TAT AAT TAT GGA CCT TCA CCC TAC ATG ACC CCA CCA TAC TGG       1344
Thr Tyr Tyr Asn Tyr Gly Pro Ser Pro Tyr Met Thr Pro Pro Tyr Trp
            435                 440                 445

GGT TTT CCA CAT CCT ACA AAT TCT GGT GGG GAT AGT CCA CGT GGA CCC       1392
```

```
                                                                              -continued Gly Phe Pro His Pro Thr Asn Ser Gly Gly Asp Ser Pro Arg Gly Pro
    450                 455                 460

CAA TCT CCT CTG GAC CTA GAC AAC ATG TTA CGG GCC ATG CCA CCC AAC          1440
Gln Ser Pro Leu Asp Leu Asp Asn Met Leu Arg Ala Met Pro Pro Asn
465                 470                 475                 480

AAG AGT GTG TTT GAT GTG TTG ACA AGT CAC CCA GGT GAC CTC GTC CAT          1488
Lys Ser Val Phe Asp Val Leu Thr Ser His Pro Gly Asp Leu Val His
                485                 490                 495

CCG TCC TTC CTC AGT CAA TGC TTG GGC AGC AGT GGT TCC CCG TAC CCA          1536
Pro Ser Phe Leu Ser Gln Cys Leu Gly Ser Ser Gly Ser Pro Tyr Pro
            500                 505                 510

AGC AGA CAA GGC CTT ATG TAGAGACGGA GGCCTCCTGG CCTGACCTGG AGTGGACA        1592
Ser Arg Gln Gly Leu Met
        515

CTCAATGAAA TGA                                                           1605

(2) INFORMATION FOR SEQ ID NO:11:

(i) SEQUENCE CHARACTERISTICS:
        (A) LENGTH: 534 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Xenopus FAST-1

(xi) SEQUENCE DESCRIPTION: SEQ ID NO:11:

Met Arg Asp Pro Ser Ser Leu Tyr Ser Gly Phe Pro Ala Gly Ser Gln
1               5                   10                  15

Tyr Glu Ser Val Glu Pro Pro Ser Leu Ala Leu Leu Ser Ser Ile Asp
                20                  25                  30

Gln Glu Gln Leu Pro Val Ala Thr Gly Gln Ser Tyr Asn His Ser Val
            35                  40                  45

Gln Pro Trp Pro Gln Pro Trp Pro Leu Ser Leu Tyr Arg Glu Gly
    50                  55                  60

Gly Thr Trp Ser Pro Asp Arg Gly Ser Met Tyr Gly Leu Ser Pro Gly
65                  70                  75                  80

Thr His Glu Gly Ser Cys Thr His Thr His Glu Gly Pro Lys Asp Ser
                85                  90                  95

Met Ala Gly Asp Gln Thr Arg Ser Arg Lys Ser Lys Lys Asn Tyr
                100                 105                 110

His Arg Tyr Asn Lys Pro Pro Tyr Ser Tyr Leu Ala Met Ile Ala Leu
            115                 120                 125

Val Ile Gln Asn Ser Pro Glu Lys Arg Leu Lys Leu Ser Gln Ile Leu
    130                 135                 140

Lys Glu Val Ser Thr Leu Phe Pro Phe Phe Asn Gly Asp Tyr Met Gly
145                 150                 155                 160

Trp Lys Asp Ser Ile Arg His Asn Leu Ser Ser Ser Asp Cys Phe Lys
                165                 170                 175

Lys Ile Leu Lys Asp Pro Gly Lys Pro Gln Ala Lys Gly Asn Phe Trp
            180                 185                 190

Thr Val Asp Val Ser Arg Ile Pro Leu Asp Ala Met Lys Leu Gln Asn
    195                 200                 205

Thr Ala Leu Thr Arg Gly Gly Ser Asp Tyr Phe Val Gln Asp Leu Ala
```

```
            210                 215                 220
Pro Tyr Ile Leu His Asn Tyr Lys Tyr Glu His Asn Ala Gly Ala Tyr
225                 230                 235                 240

Gly His Gln Met Pro Pro Ser His Ala Arg Ser Leu Ser Leu Ala Glu
                245                 250                 255

Asp Ser Gln Gln Thr Asn Thr Gly Gly Lys Leu Asn Thr Ser Phe Met
                260                 265                 270

Ile Asp Ser Leu Leu His Asp Leu Gln Glu Val Asp Leu Pro Asp Ala
                275                 280                 285

Ser Arg Asn Leu Glu Asn Gln Arg Ile Ser Pro Ala Val Ala Met Asn
290                 295                 300

Asn Met Trp Ser Ser Ala Pro Leu Leu Tyr Thr His Ser Lys Pro Thr
305                 310                 315                 320

Arg Asn Ala Arg Ser Pro Gly Leu Ser Thr Ile His Ser Thr Tyr Ser
                325                 330                 335

Ser Ser Ser Ser Ser Ile Ser Thr Ile Ser Pro Val Gly Phe Gln Lys
                340                 345                 350

Glu Gln Glu Lys Ser Gly Arg Gln Thr Gln Arg Val Gly His Pro Ile
                355                 360                 365

Lys Arg Ser Arg Glu Asp Asp Asp Cys Ser Thr Thr Ser Ser Asp Pro
370                 375                 380

Asp Thr Gly Asn Tyr Ser Pro Ile Glu Pro Pro Lys Lys Met Pro Leu
385                 390                 395                 400

Leu Ser Leu Asp Leu Pro Thr Ser Tyr Thr Lys Ser Val Ala Pro Asn
                405                 410                 415

Val Val Ala Pro Pro Ser Val Leu Pro Phe Phe His Phe Pro Arg Phe
                420                 425                 430

Thr Tyr Tyr Asn Tyr Gly Pro Ser Pro Tyr Met Thr Pro Pro Tyr Trp
                435                 440                 445

Gly Phe Pro His Pro Thr Asn Ser Gly Gly Asp Ser Pro Arg Gly Pro
                450                 455                 460

Gln Ser Pro Leu Asp Leu Asp Asn Met Leu Arg Ala Met Pro Pro Asn
465                 470                 475                 480

Lys Ser Val Phe Asp Val Leu Thr Ser His Pro Gly Asp Leu Val His
                485                 490                 495

Pro Ser Phe Leu Ser Gln Cys Leu Gly Ser Ser Gly Ser Pro Tyr Pro
                500                 505                 510

Ser Arg Gln Gly Leu Met Tyr Arg Arg Pro Pro Gly Leu Thr Trp
                515                 520                 525

Ser Gly His Ser Met Lys
    530

(2) INFORMATION FOR SEQ ID NO:12:

(i) SEQUENCE CHARACTERISTICS:
        (A) LENGTH: 155 amino acids
        (B) TYPE: amino acid
        (C) STRANDEDNESS: single
        (D) TOPOLOGY: linear (ix) FEATURE:
        (A) NAME/KEY: Other
        (B) LOCATION: 1...1
        (D) OTHER INFORMATION: Xenopus FAST-1 SID (xi) SEQUENCE DESCRIPTION: SEQ ID NO:12:

Thr Ser Ser Asp Pro Asp Thr Gly Asn Tyr Ser Pro Ile Glu Pro Pro
```

```
  1               5                   10                  15
Lys Lys Met Pro Leu Leu Ser Leu Asp Leu Pro Thr Ser Tyr Thr Lys
                20                  25                  30

Ser Val Ala Pro Asn Val Val Ala Pro Pro Ser Val Leu Pro Phe Phe
                35                  40                  45

His Phe Pro Arg Phe Thr Tyr Tyr Asn Tyr Gly Pro Ser Pro Tyr Met
    50                  55                  60

Thr Pro Pro Tyr Trp Gly Phe Pro His Pro Thr Asn Ser Gly Gly Asp
65                  70                  75                  80

Ser Pro Arg Gly Pro Gln Ser Pro Leu Asp Leu Asp Asn Met Leu Arg
                85                  90                  95

Ala Met Pro Pro Asn Lys Ser Val Phe Asp Val Leu Thr Ser His Pro
                100                 105                 110

Gly Asp Leu Val His Pro Ser Phe Leu Ser Gln Cys Leu Gly Ser Ser
            115                 120                 125

Gly Ser Pro Tyr Pro Ser Arg Gln Gly Leu Met Tyr Arg Arg Arg Pro
        130                 135                 140

Pro Gly Leu Thr Trp Ser Gly His Ser Met Lys
145                 150                 155
```

(2) INFORMATION FOR SEQ ID NO:13:

(i) SEQUENCE CHARACTERISTICS:
        (A) LENGTH: 1634 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Other
        (B) LOCATION: 1...1
        (D) OTHER INFORMATION: Human FAST-1 coding region (xi) SEQUENCE DESCRIPTION: SEQ ID NO:13:

```
ATGGGGCCCT GCAGCGGCTC CCGCCTGGGG CCCCCAGAGG CTGAGTCGCC CTCCCAGCCC    60

CCTAAGAGGA GGAAGAAGAG GTACCTGCGA CATGACAAGC CCCCCTACAC CTACTTGGCC   120

ATGATCGCCT TGGTGATTCA GGCCGCTCCC TCCCGCAGAC TGAAGCTGGC CCAGATCATC   180

CGTCAGGTCC AGGCCGTGTT CCCCTTCTTC AGGGAAGACT ACGAGGGCTG AAAGACTCC    240

ATTCGCCACA ACCTTTCCTC AACCGATGC TTCCGCAAGG TGCCCAAGGA CCCTGCAAAG    300

CCCCAGGCCA AGGCAACTT CTGGGCGGTC GACGTGAGCC TGATCCCAGC TGAGGCGCTC    360

CGGCTGCAGA ACACCGCCCT GTGCCGGCGC TGGCAGAACG GAGGTGCGCG TGGAGCCTTC   420

GCCAAGGACC TGGGCCCCTA CGTGCTGCAC GGCCGGCCAT ACCGGCCGCC CAGTCCCCCG   480

CCACCACCCA GTGAGGGCTT CAGCATCAAG TCCCTGCTAA GAAGGTCCGG GGAAGGGGCA   540

CCCTGGCCGG GGCTAGCTCC ACAGAACAGC CCAGTTCCTG CAGGCACAGG GAACAATGGG   600

GAAGAAGCGG TGCCCACCCC ACCCCTTCCC TCTTCTGAAA GGCCTCTGTG CCCCTCTGC    660

CCCCTTCCTG GCCCCACGAG AGTGGAGGGG GAGACTGTGC AGGGGGGAGC CATGGGCCCT   720

CAACCCTCTC CCCAGAGCCT AGGGCCTGGC CTTTCCACTA CTGCAGGGCA CCGCAGTTCT   780

GGGGGACGGT CCAGCGGGGG ACACAGGGCC TCCCTTTGGG GGCAGCTGCC CACCTCCTAC   840

TTGCCTATCT ACACTCCCAA TGTGGTAATG CCCTTGGCAC CACCACCCAC CTCCTGTCCC   900

CAGTGTCCGT CAACCAGCCC TGCCTACTGG GGGTGGCCCC CTGAAACCCG AGGGCCCCCA   960
```

-continued

```
GGGCTGCTCT GCGATCTAAA CGCCCTCTTC CAAGGGGTGC CACCCAACAA AAGCATCTAC    1020

GACGTTTGGG TCAGCCACCC TCGGGACCTG GCGGCCCCTG GCCCAGGCTG GCTGCTCTCC    1080

TGGTGCAGCC TGTGAGGCTC TTAAGACAGG GGCCGCTCCT CCCTCCCGCT CCCACCCCCA    1140

CCTTGTTGAC AGGGAGCCAA GGCGAGGCGG CTGTCTGCGA CCACAGCAGC CTCGAAACAC    1200

CAGGCAGCAG CCTTGCTGGG AGTCCACGGT GTTTATTGGG CCACCCCACG CATGGCCGTG    1260

GCCCAGCTGG GCACAACCCT CACCCTGGTC TGTCATGCCT GTTTTTCCTA CACTCAGCGG    1320

CAAAACTGCA GGAGCAGGCT GAACCTGAAT ATCCCTTCCT AATCCCTCTT CTCAGCCCAC    1380

TACCCATCCA TCAGTCACCA GCCGTCACCT CCCTCCCGTG CTCCAGCTGG GGAAGGAAA    1440

ACCCATGTGG ATCACCTGAA ATCCTGCCCT CTCTCTCTGT CGGAAAAGAA GTCCACCTTT    1500

TTCCGGAAAC CGGTTAGGGA ATTAAAATGC CTACATGTC CTGGTGGTTG GGGGGAAAC     1560

CACTAAAGGA ATTTGCAACC TTTTTTATCC TCTTTCATTT ATCCCAAGGG GGGGCCCGTC    1620

CCATTTCCCC AACC                                                      1634
```

(2) INFORMATION FOR SEQ ID NO:14:

(i) SEQUENCE CHARACTERISTICS:
        (A) LENGTH: 544 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Human FAST-1

(xi) SEQUENCE DESCRIPTION: SEQ ID NO:14:

```
Met Gly Pro Cys Ser Gly Ser Arg Leu Gly Pro Pro Glu Ala Glu Ser
 1               5                  10                  15

Pro Ser Gln Pro Pro Lys Arg Arg Lys Lys Arg Tyr Leu Arg His Asp
            20                  25                  30

Lys Pro Pro Tyr Thr Tyr Leu Ala Met Ile Ala Leu Val Ile Gln Ala
        35                  40                  45

Ala Pro Ser Arg Arg Leu Lys Leu Ala Gln Ile Ile Arg Gln Val Gln
    50                  55                  60

Ala Val Phe Pro Phe Phe Arg Glu Asp Tyr Glu Gly Trp Lys Asp Ser
65                  70                  75                  80

Ile Arg His Asn Leu Ser Ser Asn Arg Cys Phe Arg Lys Val Pro Lys
                85                  90                  95

Asp Pro Ala Lys Pro Gln Ala Lys Gly Asn Phe Trp Ala Val Asp Val
            100                 105                 110

Ser Leu Ile Pro Ala Glu Ala Leu Arg Leu Gln Asn Thr Ala Leu Cys
        115                 120                 125

Arg Arg Trp Gln Asn Gly Gly Ala Arg Gly Ala Phe Ala Lys Asp Leu
    130                 135                 140

Gly Pro Tyr Val Leu His Gly Arg Pro Tyr Arg Pro Ser Pro Pro
145                 150                 155                 160

Pro Pro Pro Ser Glu Gly Phe Ser Ile Lys Ser Leu Leu Arg Arg Ser
                165                 170                 175

Gly Glu Gly Ala Pro Trp Pro Gly Leu Ala Pro Gln Asn Ser Pro Val
            180                 185                 190

Pro Ala Gly Thr Gly Asn Asn Gly Glu Glu Ala Val Pro Thr Pro Pro
```

```
                195                 200                 205
Leu Pro Ser Ser Glu Arg Pro Leu Trp Pro Leu Cys Pro Leu Pro Gly
        210                 215                 220

Pro Thr Arg Val Glu Gly Glu Thr Val Gln Gly Ala Met Gly Pro
225                 230                 235                 240

Gln Pro Ser Pro Gln Ser Leu Gly Pro Gly Leu Ser Thr Thr Ala Gly
                245                 250                 255

His Arg Ser Ser Gly Gly Arg Ser Ser Gly Gly His Arg Ala Ser Leu
            260                 265                 270

Trp Gly Gln Leu Pro Thr Ser Tyr Leu Pro Ile Tyr Thr Pro Asn Val
                275                 280                 285

Val Met Pro Leu Ala Pro Pro Thr Ser Cys Pro Gln Cys Pro Ser
290                 295                 300

Thr Ser Pro Ala Tyr Trp Gly Val Ala Pro Glu Thr Arg Gly Pro Pro
305                 310                 315                 320

Gly Leu Leu Cys Asp Leu Asn Ala Leu Phe Gln Gly Val Pro Pro Asn
                325                 330                 335

Lys Ser Ile Tyr Asp Val Trp Val Ser His Pro Arg Asp Leu Ala Ala
                340                 345                 350

Pro Gly Pro Gly Trp Leu Leu Ser Trp Cys Ser Leu Glx Gly Ser Glx
                355                 360                 365

Asp Arg Gly Arg Ser Ser Leu Pro Leu Pro Pro Pro Cys Glx Gln
370                 375                 380

Gly Ala Lys Ala Arg Arg Leu Ser Ala Thr Thr Ala Ala Ser Lys His
385                 390                 395                 400

Gln Ala Ala Ala Leu Leu Gly Val His Gly Val Tyr Trp Ala Thr Pro
                405                 410                 415

Arg Met Ala Val Ala Gln Leu Gly Thr Thr Leu Thr Leu Val Cys His
                420                 425                 430

Ala Cys Phe Ser Tyr Thr Gln Arg Gln Asn Cys Arg Ser Arg Leu Asn
            435                 440                 445

Leu Asn Ile Pro Ser Glx Ser Leu Phe Ser Ala His Tyr Pro Ser Ile
    450                 455                 460

Ser His Gln Pro Ser Pro Pro Ser Arg Ala Pro Ala Gly Gly Arg Lys
465                 470                 475                 480

Thr His Val Asp His Leu Lys Ser Cys Pro Leu Ser Leu Ser Glu Lys
                485                 490                 495

Lys Ser Thr Phe Phe Arg Lys Pro Val Arg Glu Leu Lys Cys Pro Thr
                500                 505                 510

Cys Pro Gly Gly Trp Gly Gly Asn His Glx Arg Asn Leu Gln Pro Phe
                515                 520                 525

Leu Ser Ser Phe Ile Tyr Pro Lys Gly Gly Pro Val Pro Phe Pro Gln
530                 535                 540

(2) INFORMATION FOR SEQ ID NO:15:

(i) SEQUENCE CHARACTERISTICS:
        (A) LENGTH: 311 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
```

(D) OTHER INFORMATION: Human FAST-1 SID (xi) SEQUENCE DESCRIPTION: SEQ ID NO:15:

```
Gln Gly Gly Ala Met Gly Pro Gln Pro Ser Pro Gln Ser Leu Gly Pro
  1               5                  10                  15
Gly Leu Ser Thr Thr Ala Gly His Arg Ser Ser Gly Gly Arg Ser Ser
             20                  25                  30
Gly Gly His Arg Ala Ser Leu Trp Gly Gln Leu Pro Thr Ser Tyr Leu
         35                  40                  45
Pro Ile Tyr Thr Pro Asn Val Val Met Pro Leu Ala Pro Pro Pro Thr
     50                  55                  60
Ser Cys Pro Gln Cys Pro Ser Thr Ser Pro Ala Tyr Trp Gly Val Ala
 65                  70                  75                  80
Pro Glu Thr Arg Gly Pro Pro Gly Leu Leu Cys Asp Leu Asn Ala Leu
                 85                  90                  95
Phe Gln Gly Val Pro Pro Asn Lys Ser Ile Tyr Asp Val Trp Val Ser
                100                 105                 110
His Pro Arg Asp Leu Ala Ala Pro Gly Pro Gly Trp Leu Leu Ser Trp
            115                 120                 125
Cys Ser Leu Glx Gly Ser Glx Asp Arg Gly Arg Ser Ser Leu Pro Leu
130                 135                 140
Pro Pro Pro Cys Glx Gln Gly Ala Lys Ala Arg Arg Leu Ser Ala
145                 150                 155                 160
Thr Thr Ala Ala Ser Lys His Gln Ala Ala Ala Leu Leu Gly Val His
                165                 170                 175
Gly Val Tyr Trp Ala Thr Pro Arg Met Ala Val Ala Gln Leu Gly Thr
            180                 185                 190
Thr Leu Thr Leu Val Cys His Ala Cys Phe Ser Tyr Thr Gln Arg Gln
        195                 200                 205
Asn Cys Arg Ser Arg Leu Asn Leu Asn Ile Pro Ser Glx Ser Leu Phe
210                 215                 220
Ser Ala His Tyr Pro Ser Ile Ser His Gln Pro Ser Pro Ser Arg
225                 230                 235                 240
Ala Pro Ala Gly Gly Arg Lys Thr His Val Asp His Leu Lys Ser Cys
                245                 250                 255
Pro Leu Ser Leu Ser Glu Lys Lys Ser Thr Phe Phe Arg Lys Pro Val
                260                 265                 270
Arg Glu Leu Lys Cys Pro Thr Cys Pro Gly Gly Trp Gly Gly Asn His
            275                 280                 285
Glx Arg Asn Leu Gln Pro Phe Leu Ser Ser Phe Ile Tyr Pro Lys Gly
        290                 295                 300
Gly Pro Val Pro Phe Pro Gln
305                 310
```

(2) INFORMATION FOR SEQ ID NO:16:

(i) SEQUENCE CHARACTERISTICS:
      (A) LENGTH: 1668 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Other
      (B) LOCATION: 1...1
      (D) OTHER INFORMATION: Mouse FAST-1 coding region (xi) SEQUENCE DESCRIPTION: SEQ ID NO:16:

```
ATGGCCTCGG GCTGGGACCT GGCCTCAACT TACACTCCGA CTACCCCGAG CCCCCAGTTA      60
GCCCTGGCTC CGGCCCAGGG CTACCTCCCT TGTATGGGGC CTCGCGACAA CTCTCAGCTG     120
AGGCCTCCAG AGGCAGAGTC TCTTTCGAAG ACCCCCAAGA GGAGGAAGAA GAGATACCTA     180
CGGCATGACA AGCCCCCCTA CACCTACTTG GCCATGATCG CCTTGGTAAT TCAGGCCGCA     240
CCCTTCCGCA GGCTGAAACT GGCTCAGGTC CAGGCAGTGT TCCCCTTCTT CAGGGACGAC     300
TATGAGGGCT GGAAGGACTC CATCCGCCAC AACCTTTCCT CTAATCGGTG CTTCCATAAG     360
GTGCCCAAGG ACCCTGCAAA GCCCCAGGCC AAGGGCAACT TCTGGGCGGT GGATGTTAGC     420
CTGATTCCTG CTGAGGCGCT GCGCCTTCAG AACACTGCCC TGTGCCGTCG ATGGCAGAAC     480
CGGGGCACCC ACAGAGCTTT CGCCAAGGAC CTGAGCCCCT ACGTGCTCCA CGGCCAGCCT     540
TATCAGCCAC CCAGTCCCCC ACCACCACCT AGGGAGGGTT TCAGCATCAA GTCCCTGCTA     600
GGGGACCCTG GGAAAGAATC CACATGGCCC CAGCATCCTG GGCTCCCTGG ACAGAGCACT     660
GCAGCTCAGG CAGGCACCTT GTCAAAGGGG AAGAAGGGA TGGGCACTGG ACCCTCTAGC      720
TCCTCTGAGA CGCCTCTGTG GCCCCTCTGC TCCCTTCCTG GGCCCACAAT CATAGAGGGG     780
GAGAGTTCCC AAGGGGAGGT AATCAGGCCT TCTCCCGTCA CCCCAGATCA AGGCTCCTGG     840
CCCCTCCACT TACTTGAGGA TTCCGCAGAT TCCAGGGGAG TGCCCAGGAG GGGGAGCAGA     900
GCCTCCTTGT GGGGACAGCT ACCCACTTCT TACTTGCCCA TCTATACGCC CAATGTAGTA     960
ATGCCCTTGG CCACACTACC GACCACCTCT TGTCCCCAGT GCCCATCTTC TGCCAGCCCA    1020
GCTTACTGGA GCGTAGGCAC TGAATCCCAA GGGTCCCAGG ACCTGCTCTG TGATCTAGAC    1080
TCCCTCTTCC AGGGAGTACC ACCCAACAAG AGTATCTATG ATGTGTGGGT CAGCCATCCT    1140
AGGGACCTGG CAGCTCCTGC CCCAGGCTGG CTCCTTTCCT GGTACAGCAT GTAATATTCT    1200
AGGGCAGAAA GGGCTGTTCT CTCTTCCACC CATGAATATC ATTTTGATGA ACCAGAGCTA    1260
GGACGATGTC CCGACGGACA GCTTTAAAAC ACCAGCACAG CCTTGCTGAA ACCCACAGC     1320
TTTAATTAGG TTACTCCAGA AAGGGTTGTC TCTGCTAGAT AGGGAGGTCT GGCCAATCGT    1380
GCCAGGAGCG GAGCTCAGCC TGTAGAGTGC CTCCTCTTGA TCCTACCTTT TCAGGCCCTC    1440
AAGCCATCCA TCTATCCATC CCTCTGTCAC CATGCCTTCC TGGCTCCAGG CTGGGGGAG     1500
GGAGAGCCAA AAGTGGGTCT GATCTGAAGT CTTGCCCTCT CTCAAATGCC TGGGTAGAGG    1560
GTAGCACCTT TCAGGGAAAG GGTTAAGAAA TGAAAGACTG GAACGGACAT AATTTTGGTG    1620
TAATGGAAGT AGGGGAGCGA TTAATAGTAA AGGAATTTAC AACATTTT                 1668
```

(2) INFORMATION FOR SEQ ID NO:17:

(i) SEQUENCE CHARACTERISTICS:
        (A) LENGTH: 397 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Mouse FAST-1

(xi) SEQUENCE DESCRIPTION: SEQ ID NO:17:

```
Met Ala Ser Gly Trp Asp Leu Ala Ser Thr Tyr Thr Pro Thr Thr Pro
 1               5                  10                  15
```

```
Ser Pro Gln Leu Ala Leu Ala Pro Ala Gln Tyr Leu Pro Cys Met
         20                  25                  30

Gly Pro Arg Asp Asn Ser Gln Leu Arg Pro Pro Glu Ala Glu Ser Leu
         35                  40                  45

Ser Lys Thr Pro Lys Arg Arg Lys Arg Tyr Leu Arg His Asp Lys
50                  55                  60

Pro Pro Tyr Thr Tyr Leu Ala Met Ile Ala Leu Val Ile Gln Ala Ala
65                  70                  75                  80

Pro Phe Arg Arg Leu Lys Leu Ala Gln Val Gln Ala Val Phe Pro Phe
                 85                  90                  95

Phe Arg Asp Asp Tyr Glu Gly Trp Lys Asp Ser Ile Arg His Asn Leu
                100                 105                 110

Ser Ser Asn Arg Cys Phe His Lys Val Pro Lys Asp Pro Ala Lys Pro
             115                 120                 125

Gln Ala Lys Gly Asn Phe Trp Ala Val Asp Val Ser Leu Ile Pro Ala
         130                 135                 140

Glu Ala Leu Arg Leu Gln Asn Thr Ala Leu Cys Arg Arg Trp Gln Asn
145                 150                 155                 160

Arg Gly Thr His Arg Ala Phe Ala Lys Asp Leu Ser Pro Tyr Val Leu
                 165                 170                 175

His Gly Gln Pro Tyr Gln Pro Ser Pro Pro Pro Pro Arg Glu
                180                 185                 190

Gly Phe Ser Ile Lys Ser Leu Leu Gly Asp Pro Gly Lys Glu Ser Thr
         195                 200                 205

Trp Pro Gln His Pro Gly Leu Pro Gly Gln Ser Thr Ala Ala Gln Ala
210                 215                 220

Gly Thr Leu Ser Lys Gly Glu Glu Gly Met Gly Thr Gly Pro Ser Ser
225                 230                 235                 240

Ser Ser Glu Thr Pro Leu Trp Pro Leu Cys Ser Leu Pro Gly Pro Thr
                245                 250                 255

Ile Ile Glu Gly Glu Ser Ser Gln Gly Glu Val Ile Arg Pro Ser Pro
             260                 265                 270

Val Thr Pro Asp Gln Gly Ser Trp Pro Leu His Leu Leu Glu Asp Ser
         275                 280                 285

Ala Asp Ser Arg Gly Val Pro Arg Arg Gly Ser Arg Ala Ser Leu Trp
         290                 295                 300

Gly Gln Leu Pro Thr Ser Tyr Leu Pro Ile Tyr Thr Pro Asn Val Val
305                 310                 315                 320

Met Pro Leu Ala Thr Leu Pro Thr Thr Ser Cys Pro Gln Cys Pro Ser
                325                 330                 335

Ser Ala Ser Pro Ala Tyr Trp Ser Val Gly Thr Glu Ser Gln Gly Ser
             340                 345                 350

Gln Asp Leu Leu Cys Asp Leu Asp Ser Leu Phe Gln Gly Val Pro Pro
         355                 360                 365

Asn Lys Ser Ile Tyr Asp Val Trp Val Ser His Pro Arg Asp Leu Ala
         370                 375                 380

Ala Pro Ala Pro Gly Trp Leu Leu Ser Trp Tyr Ser Met
385                 390                 395

(2) INFORMATION FOR SEQ ID NO:18:

(i) SEQUENCE CHARACTERISTICS:
        (A) LENGTH: 88 amino acids
        (B) TYPE: amino acid
```

```
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Mouse FAST-1 SID (xi) SEQUENCE DESCRIPTION: SEQ ID NO:18:

Ser Tyr Leu Pro Ile Tyr Thr Pro Asn Val Val Met Pro Leu Ala Thr
1               5                  10                  15

Leu Pro Thr Thr Ser Cys Pro Gln Cys Pro Ser Ser Ala Ser Pro Ala
            20                  25                  30

Tyr Trp Ser Val Gly Thr Glu Ser Gln Gly Ser Gln Asp Leu Leu Cys
        35                  40                  45

Asp Leu Asp Ser Leu Phe Gln Gly Val Pro Pro Asn Lys Ser Ile Tyr
    50                  55                  60

Asp Val Trp Val Ser His Pro Arg Asp Leu Ala Ala Pro Ala Pro Gly
65                  70                  75                  80

Trp Leu Leu Ser Trp Tyr Ser Met
                85
```